(12) United States Patent
Higgins et al.

(10) Patent No.: US 10,667,679 B2
(45) Date of Patent: Jun. 2, 2020

(54) IMAGE-BASED GLOBAL REGISTRATION SYSTEM AND METHOD APPLICABLE TO BRONCHOSCOPY GUIDANCE

(71) Applicant: The Penn State Research Foundation, University Park, PA (US)

(72) Inventors: William E. Higgins, State College, PA (US); Rahul Khare, Pittsburgh, PA (US); Scott A. Merritt, Golden, CO (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/928,974

(22) Filed: Mar. 22, 2018

(65) Prior Publication Data
US 2018/0220883 A1 Aug. 9, 2018

Related U.S. Application Data

(63) Continuation of application No. 13/016,093, filed on Jan. 28, 2011, now abandoned.
(Continued)

(51) Int. Cl.
*A61B 1/267* (2006.01)
*A61B 1/00* (2006.01)
(Continued)

(52) U.S. Cl.
CPC ........ *A61B 1/2676* (2013.01); *A61B 1/00009* (2013.01); *G06K 9/00208* (2013.01);
(Continued)

(58) Field of Classification Search
CPC .... A61B 1/2676; G06T 7/75; G06K 9/00208; G06K 9/00214; G06K 9/6206
(Continued)

(56) References Cited

U.S. PATENT DOCUMENTS 5,704,897 A * 1/1998 Truppe ................. A61B 1/0005
128/922
5,782,762 A * 7/1998 Vining ................. G06T 7/0012
128/920
(Continued)

FOREIGN PATENT DOCUMENTS

JP 2000-135215 5/2000

OTHER PUBLICATIONS

A. D. Sihoe and A. P. Yim, "Lung cancer staging," J. Surgical Research, vol. 117, No. 1, pp. 92-106, Mar. 2004.
(Continued)

*Primary Examiner* — Timothy J Neal
*Assistant Examiner* — Jae Woo
(74) *Attorney, Agent, or Firm* — Dinsmore & Shohl LLP

(57) ABSTRACT

A global registration system and method identifies bronchoscope position without the need for significant bronchoscope maneuvers, technician intervention, or electromagnetic sensors. Virtual bronchoscopy (VB) renderings of a 3D airway tree are obtained including VB views of branch positions within the airway tree. At least one real bronchoscopic (RB) video frame is received from a bronchoscope inserted into the airway tree. An algorithm according to the invention is executed on a computer to identify the several most likely branch positions having a VB view closest to the received RB view, and the 3D position of the bronchoscope within the airway tree is determined in accordance with the branch position identified in the VB view. The preferred embodiment involves a fast local registration search over all the branches in a global airway-bifurcation search space, with the weighted normalized sum of squares distance metric used for finding the best match.

11 Claims, 24 Drawing Sheets

Related U.S. Application Data

(60) Provisional application No. 61/300,969, filed on Feb. 3, 2010, provisional application No. 61/299,194, filed on Jan. 28, 2010.

(51) Int. Cl.
*G06T 7/73* (2017.01)
*G06K 9/00* (2006.01)
*G06K 9/62* (2006.01)

(52) U.S. Cl.
CPC ....... *G06K 9/00214* (2013.01); *G06K 9/6206* (2013.01); *G06T 7/75* (2017.01); *G06T 2207/10068* (2013.01); *G06T 2207/30061* (2013.01)

(58) Field of Classification Search
USPC .......................................................... 600/117
See application file for complete search history.

(56) References Cited

U.S. PATENT DOCUMENTS

| | | | | |
|---|---|---|---|---|
| 6,505,065 | B1* | 1/2003 | Yanof | A61N 5/103 600/103 |
| 6,892,090 | B2* | 5/2005 | Verard | A61B 34/20 600/424 |
| 6,930,706 | B2* | 8/2005 | Kobayashi | A61B 1/042 348/65 |
| 7,144,367 | B2* | 12/2006 | Chen | A61B 1/00009 600/117 |
| 7,300,398 | B2* | 11/2007 | Chefd'hotel | G06T 7/33 382/128 |
| 7,623,900 | B2* | 11/2009 | Graham | G06T 19/003 382/128 |
| 7,641,609 | B2* | 1/2010 | Ohnishi | A61B 1/00009 600/117 |
| 7,659,912 | B2* | 2/2010 | Akimoto | A61B 1/00009 345/420 |
| 7,756,563 | B2* | 7/2010 | Higgins | A61B 1/00009 600/407 |
| 7,811,294 | B2* | 10/2010 | Strommer | A61B 1/00147 606/108 |
| 7,889,905 | B2* | 2/2011 | Higgins | A61B 1/00147 382/130 |
| 7,901,348 | B2* | 3/2011 | Soper | A61B 1/0008 600/117 |
| 7,929,014 | B2* | 4/2011 | Akimoto | A61B 1/00009 348/65 |
| 7,940,967 | B2* | 5/2011 | Ozaki | A61B 1/00009 382/128 |
| 7,951,070 | B2* | 5/2011 | Ozaki | A61B 1/00009 600/104 |
| 7,985,187 | B2* | 7/2011 | Wibowo | A61B 5/02007 600/529 |
| 7,998,062 | B2* | 8/2011 | Gilboa | A61B 1/00154 600/117 |
| 8,009,167 | B2* | 8/2011 | Dekel | G06T 15/08 345/419 |
| 8,023,712 | B2* | 9/2011 | Ikuma | A61B 5/06 382/128 |
| 8,049,777 | B2* | 11/2011 | Akimoto | A61B 1/2676 348/65 |
| 8,064,669 | B2* | 11/2011 | Higgins | A61B 1/00147 382/130 |
| 8,102,416 | B2* | 1/2012 | Ito | A61B 34/20 348/65 |
| 8,199,984 | B2* | 6/2012 | Mori | A61B 6/466 382/128 |
| 8,202,213 | B2* | 6/2012 | Ito | A61B 1/00009 600/103 |
| 8,219,179 | B2* | 7/2012 | Ganatra | A61B 34/20 382/128 |
| 8,280,136 | B2* | 10/2012 | Gotardo | G06K 9/6207 378/4 |
| 8,298,135 | B2* | 10/2012 | Ito | A61B 1/00009 600/103 |
| 2002/0118278 | A1 | 8/2002 | Kobayashi et al. | |
| 2003/0091967 | A1 | 5/2003 | Chosack et al. | |
| 2005/0020878 | A1* | 1/2005 | Ohnishi | A61B 1/00009 600/117 |
| 2005/0085717 | A1* | 4/2005 | Shahidi | A61B 1/04 600/424 |
| 2005/0107679 | A1* | 5/2005 | Geiger | G06T 19/003 600/407 |
| 2005/0122343 | A1* | 6/2005 | Bailey | G06T 3/0037 345/619 |
| 2005/0182295 | A1* | 8/2005 | Soper | A61B 1/0008 600/117 |
| 2005/0272971 | A1* | 12/2005 | Ohnishi | A61B 1/00009 600/101 |
| 2006/0149134 | A1* | 7/2006 | Soper | A61B 1/0008 600/182 |
| 2007/0013710 | A1* | 1/2007 | Higgins | A61B 1/00147 345/581 |
| 2007/0015997 | A1 | 1/2007 | Higgins et al. | |
| 2007/0142705 | A1* | 6/2007 | Ohnishi | A61B 1/00009 600/109 |
| 2007/0167714 | A1 | 7/2007 | Kiraly et al. | |
| 2007/0173689 | A1* | 7/2007 | Ozaki | A61B 1/00009 600/111 |
| 2007/0225553 | A1* | 9/2007 | Shahidi | A61B 5/064 600/103 |
| 2008/0183073 | A1* | 7/2008 | Higgins | G06T 19/003 600/425 |
| 2008/0207997 | A1* | 8/2008 | Higgins | A61B 1/00009 600/114 |
| 2008/0294000 | A1* | 11/2008 | Iwamoto | A61B 1/00048 600/103 |
| 2009/0156895 | A1* | 6/2009 | Higgins | G06T 19/003 600/104 |
| 2009/0161927 | A1 | 6/2009 | Mori et al. | |
| 2009/0209817 | A1* | 8/2009 | Averbuch | A61B 5/066 600/118 |
| 2009/0220171 | A1* | 9/2009 | Liu | A61B 6/5247 382/282 |
| 2009/0292171 | A1* | 11/2009 | Ito | A61B 1/00009 600/111 |
| 2010/0041949 | A1* | 2/2010 | Tolkowsky | A61B 1/0052 600/109 |
| 2010/0280365 | A1* | 11/2010 | Higgins | A61B 1/00009 600/424 |
| 2010/0310146 | A1* | 12/2010 | Higgins | G06T 7/162 382/131 |
| 2011/0184238 | A1* | 7/2011 | Higgins | A61B 1/00009 600/117 |
| 2011/0282151 | A1* | 11/2011 | Trovato | A61B 5/06 600/117 |
| 2012/0059220 | A1* | 3/2012 | Holsing | A61B 1/2676 600/109 |
| 2012/0082351 | A1* | 4/2012 | Higgins | A61B 1/00147 382/128 |
| 2012/0130171 | A1* | 5/2012 | Barak | A61B 1/00009 600/117 |
| 2012/0203065 | A1* | 8/2012 | Higgins | A61B 1/2676 600/109 |
| 2012/0203067 | A1* | 8/2012 | Higgins | A61B 1/00006 600/117 |
| 2012/0289777 | A1* | 11/2012 | Chopra | A61B 1/00009 600/109 |

OTHER PUBLICATIONS

J. P. Helferty, A. J. Sherbondy, A. P. Kiraly, and W. E. Higgins, "Computer-based system for the virtual-endoscopic guidance of bronchoscopy," Comput. Vis. Image Underst., vol. 108, No. 1-2, pp. 171-187, Oct.-Nov. 2007.

(56) References Cited

OTHER PUBLICATIONS

W. E. Higgins, J. P. Helferty, K. Lu, S. A. Merritt, L. Rai, and K. C. Yu, "3D CT-video fusion for image-guided bronchoscopy," Comput. Med. Imaging Graph., vol. 32, No. 3, pp. 159-173, Apr. 2008.
E. A. Kazerooni, "High resolution CT of the lungs," Am. J. Roentgenology, vol. 177, No. 3, pp. 501-519, Sep. 2001.
N. C. Dalrymple, S. R. Prasad, M. W. Freckleton, and K. N. Chintapalli, "Introduction to the language of three-dimensional imaging with multidetector CT," Radiographics, vol. 25, No. 5, pp. 1409-1428, Sep.-Oct. 2005.
U. Ueno, T. Murase, K. Yoneda, T. Tsujikawa, S. Sakiyama, and K. Kondoh, "Three-dimensional imaging of thoracic diseases with multi-detector row CT," J. Med. Invest., vol. 51, No. 3-4, pp. 163-170, Aug. 2004.
D. Osborne, P. Vock, J. Godwin, and P. Silverman, "CT identification of bronchopulmonary segments: 50 normal subjects," AJR, vol. 142, No. 1, pp. 47-52, Jan. 1984.
M. Y. Dolina, D. C. Cornish, S. A. Merritt, L. Rai, R. Mahraj, W. E. Higgins, and R. Bascom, "Interbronchoscopist variability in endobronchial path selection: a simulation study," Chest, vol. 133, No. 4, pp. 897-905, Apr. 2008.
F. Asano, Y. Matsuno, A. Tsuzuku, M. Anzai, N. Shinagawa, H. Moriya, et al., "Diagnosis of peripheral pulmonary lesions using a bronchoscope insertion guidance system combined with endobronchial ultrasonography with a guide sheath," Lung Cancer, vol. 60, No. 3, pp. 366-373, Jun. 2008.
S. B. Solomon, P. White, Jr., C. M. Wiener, J. B. Orens, and K. P. Wang, "Three-dimensionsal CT-guided bronchoscopy with a real-time electromagnetic position sensor: a comparison of two image registration methods," Chest, vol. 118, No. 6, pp. 1783-1787, Dec. 2000.
T. R. Gildea, P. J. Mazzone, D. Karnak, M. Meziane, and A. C. Mehta, "Electromagnetic navigation diagnostic bronchoscopy: a prospective study," Am. J. Resp. Crit. Care Med., vol. 174, No. 9, pp. 982-989, Nov. 1, 2006.
Y. Schwarz, J. Greif, H. D. Becker, A. Ernst, and A. Mehta, "Real-time electromagnetic navigation bronchoscopy to peripheral lung lesions using overlaid CT images: the first human study," Chest, vol. 129, No. 4, pp. 988-994, Apr. 2006.
W. E. Higgins, K. Ramaswamy, R. Swift, G. McLennan, and E. A. Hoffman, "Virtual bronchoscopy for 3D pulmonary Image assessment: State of the art and future needs," Radiographics, vol. 18, No. 3, pp. 761-778, May-Jun. 1998.
H. P. McAdams, P. C. Goodman, and P. Kussin, "Virtual bronchoscopy for directing transbronchial needle aspiration of hilar and mediastinal lymph nodes: a pilot study," Am. J. Roentgenology, vol. 170, No. 5, pp. 1361-1364, May 1998.
K. Hopper, T. Lucas, K. Gleeson, J. Stauffer, R. Bascom, D. Mauger, and R. Mahraj, "Transbronchial biopsy with virtual CT bronchoscopy and nodal highlighting," Radiology, vol. 221, No. 2, pp. 531-536, Nov. 2001.
H. D. Becker, F. Herth, A. Ernst, and Y. Schwarz, "Bronchoscopic biopsy of peripheral lung lesions under electromagnetic guidance: a pilot study," J. Bronchology, vol. 12, No. 1, pp. 9, Jan. 2005.
N. Shinagawa, K. Yamazaki, Y. Onodera, K. Miyasaka, E. Kikuchi, H. Dosaka-Akita, and M. Nishimura, "CT-guided transbronchial biopsy using an ultrathin bronchoscope with virtual bronchoscopic navigation," Chest, vol. 125, No. 3, pp. 1138-1143, Mar. 2004.
K. Mori, K. Ishitani, D. Deguchi, T. Kitasaka, Y. Suenaga, H. Takabatake, M. Mori, and H. Natori, "Compensation of electromagnetic tracking system using an optical tracker and its application to bronchoscopy navigation system," 2007, vol. 6509, p. 65090M, SPIE.
I. Wegner, J. Biederer, R. Tetzlaff, I. Wolf, and H.-P. Meinzer, "Evaluation and extension of a navigation system for bronchoscopy inside human lungs," in SPIE Medical Imaging 2007: Visualization and Image-Guided Procedures, Kevin R. Cleary and Michael I. Miga, Eds., 2007, vol. 6509, pp. 65091H1-65091H12.
T. D. Soper, D. R. Haynor, R. W. Glenny, and E. J. Seibel, "Validation of CT-video registration for guiding a novel ultrathin bronchoscope to peripheral lung nodules using electromagnetic tracking," in Society of Photo-Optical Instrumentation Engineers (SPIE) Conference Series, Feb. 2009, vol. 7261 of Society of Photo-Optical InstrumentationEngineers (SPIE) Conference Series.
K. Mori, D. Deguchi, K. Akiyama, T. Kitasaka, C. R. Maurer, Y. Suenaga, H. Takabatake, M. Mori, and H. Natori, "Hybrid bronchoscope tracking using a magnetic tracking sensor and image registration," in Medical Image Computing and Computer Assisted Intervention 2005, J. Duncan and G. Gerig, Eds., 2005, vol. LNCS 3750, pp. 543-550.
I. Bricault, G. Ferretti, and P. Cinquin, "Registration of real and CT-derived virtual bronchoscopic images to assist transbronchial biopsy," IEEE Transactions on Medical Imaging, vol. 17, No. 5, pp. 703-714, Oct. 1998.
S. A. Merritt, L. Rai, and W. E. Higgins, "Real-time CT-video registration for continuous endoscopic guidance," in SPIE Medical Imaging 2006: Physiology, Function, and Structure from Medical Images, A. Manduca and A. A. Amini, Eds., 2006, vol. 6143, pp. 370-384.
S. A. Merritt, J. D. Gibbs, K. C. Yu, V. Patel, L. Rai, D. C. Cornish, R. Bascom, and W. E. Higgins, "Real-time image-guided bronchoscopy for peripheral lung lesions: A phantom study," Chest, vol. 134, No. 5, pp. 1017-1026, Nov. 2008.
J. P. Helferty and W. E. Higgins, "Technique for registering 3D virtual CT images to endoscopic video," IEEE Int. Conf. Image Processing, vol. II, pp. 893-896, Oct. 7-10, 2001.
E-Y Kang, I. Cohen, and G. Medioni, "A graph-based global registration for 2D mosaics," in ICPR, 2000, pp. 1257-1260.
Y. Wang and Lu-ping L. Xu, "A global optimized registration algorithm for image stitching," in Image and Signal Processing, 2008. CISP '08. Congress on, May 2008, vol. 3, pp. 525-529.
Y. Li and C. Davis, "A combined global and local approach for automated registration of high-resolution satellite mages using optimum extrema points," in Geoscience and Remote Sensing Symposium, 2008. IGARSS 2008. IEEE International, Jul. 2008, vol. 2, pp. II-1032-II-1035.
A.Wong and D. Clausi, "ARRSI: Automatic registration of remote-sensing images," Geoscience and Remote Sensing, IEEE Transactions on, vol. 45, No. 5, pp. 1483-1493, May 2007.
N. Gelfand, N. J. Mitra, L. J. Guibas, and H. Pottmann, "Robust global registration," in SGP 2005: Third Eurographics Symposium on Geometry processing, Matthieu Desbrun and Helmut Pottmann, Eds. 2005, pp. 197-206, Eurographics Association.
L. Moreno, S. Garrido, and D. Blanco, "Mobile robot global localization using an evolutionary MAP filter," J. of Global Optimization, vol. 37, No. 3, pp. 381-403, 2007.
P. Jensfelt and S. Kristensen, "Active global localisation for a mobile robot using multiple hypothesis tracking," IEEE Transactions on Robotics and Automation, vol. 17, No. 5, pp. 748-760, Oct. 2001.
K. O. Arras, J. A. Castellanos, M. Schilt, and R. Siegwart, "Feature-based multi-hypothesis localization and tracking using geometric constraints," Robotics and Autonomous Systems, vol. 44, No. 1, pp. 41-53, 2003.
W. Burgard, D. Fox, D. Hennig, and T. Schmidt, "Estimating the absolute position of a mobile robot using position probability grids," in AAAI/IAAI, vol. 2, 1996.
F. Dellaert, D. Fox, W. Burgard, and S. Thrun, "Monte Carlo localization for mobile robots," in IEEE International Conference on Robotics and Automation (ICRA99), May 1999.
Z. Zhang, "Adaptive region intensity based rigid ultrasound and CT image registration," in Computer Vision and Pattern Recognition, 2008. CVPR 2008. IEEE Conference on, Jun. 2008, pp. 1-7.
H. Munim and A. Farag, "A new global registration approach of medical imaging using vector maps," in Biomedical Imaging: From Nano to Macro, 2007. ISBI 2007. 4th IEEE International Symposium on, Apr. 2007, pp. 584-587.
M. H. Moghari and P. Abolmaesumi, "Global registration of multiple bone fragments using statistical atlas models: Feasibility experiments," in Engineering in Medicine and Biology Society, 2008. EMBS 2008. 30th Annual International Conference of the IEEE, Aug. 2008, pp. 5374-5377.

(56) References Cited

OTHER PUBLICATIONS

C. Fookes, J. Williams, and M. Bennamoun, "Global 3D rigid registration of medical images," in Image Processing, 2000. Proceedings. 2000 International Conference on, 2000, vol. 2, pp. 447-450.

R. Shinohara, K. Mori, D. Deguchi, T. Kitasaka, Y. Suenaga, H. Takabatake, M. Mori, and H. Natori, "Branch identification method for CT-Guided bronchoscopy based on eigenspace image matching between real and virtual bronchoscopic images," in SPIE Medical Imaging 2006: Physiology, Function, and Structure from Medical Images, A. Manduca and A. A. Amini, Eds., Mar. 2006, vol. 6143, pp. 385-396.

J. P. Helferty, C. Zhang, G. McLennan, and W. E. Higgins, "Videoendoscopic distortion correction and its application to virtual guidance of endoscopy," IEEE Trans. Med. Imaging, vol. 20, No. 7, pp. 605-617, Jul. 2001.

W. E. Lorensen and H. E. Cline, "Marching cubes: A high resolution 3D surface construction algorithm," Computer Graphics, vol. 21, No. 4, pp. 163-169, Jul. 1987.

G. Weifi, C. Wetzler, and E. V. Puttkamer, "Keeping track of position and orientation of moving indoor systems by correlation of range-finder scans," in In Proc. 1994 IEEE Int. Conf. on Intelligent Robots and Systems IROS '94, 1994, pp. 595-601.

J. L. Bentley, F. P. Preparata, and M. G. Faust, "Approximation algorithms for convex hulls," Commun. ACM, vol. 25, No. 1, pp. 64-68, 1982.

\* cited by examiner

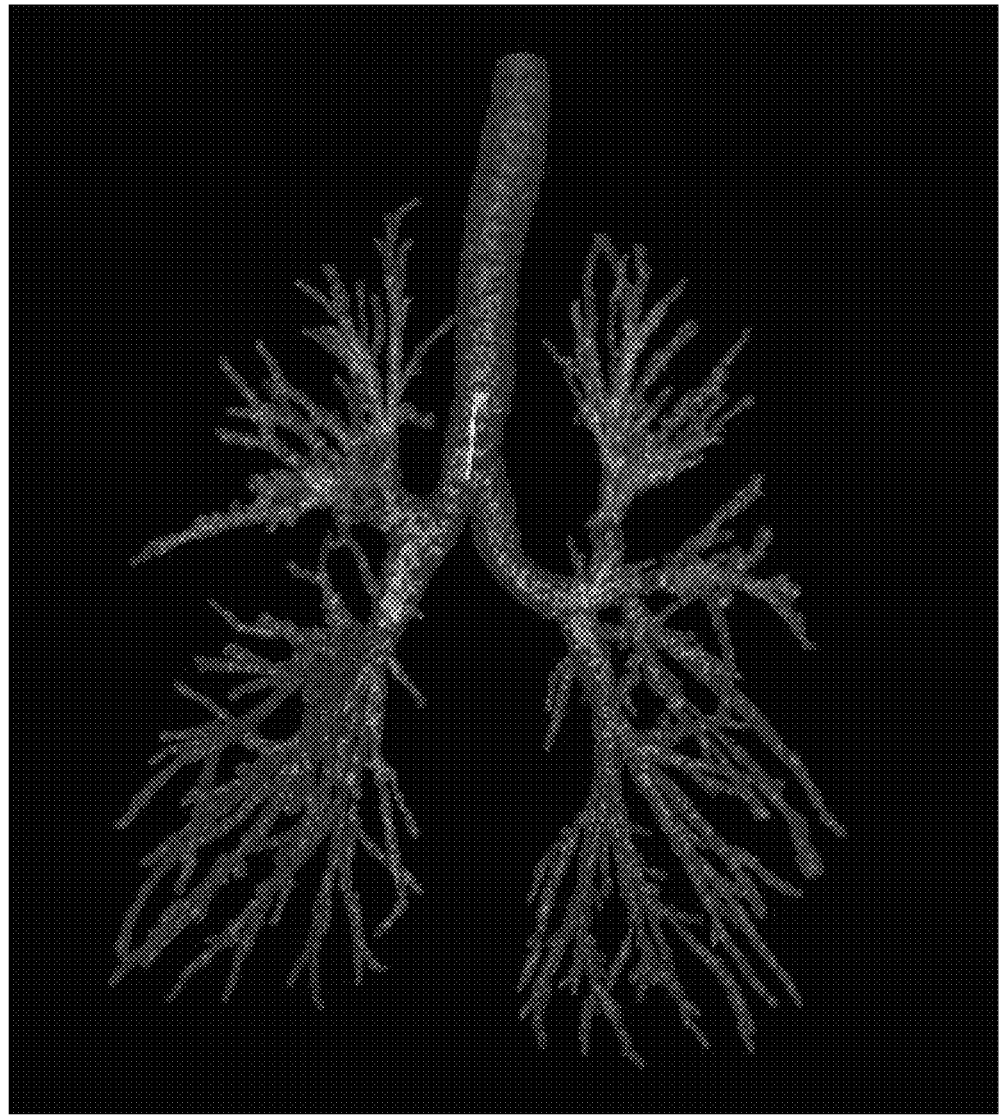
FIGURE 2A Trachea

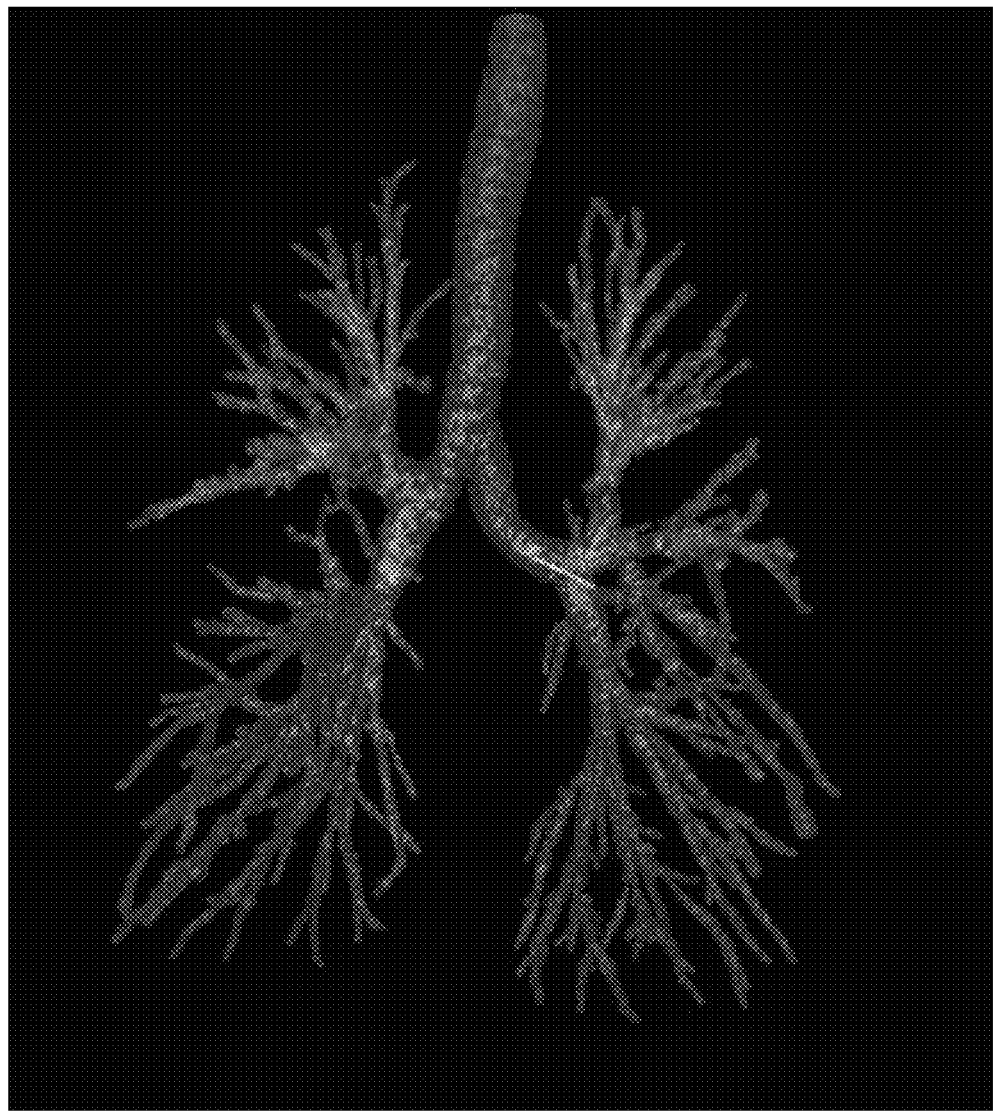
FIGURE 2B Left main bronchus

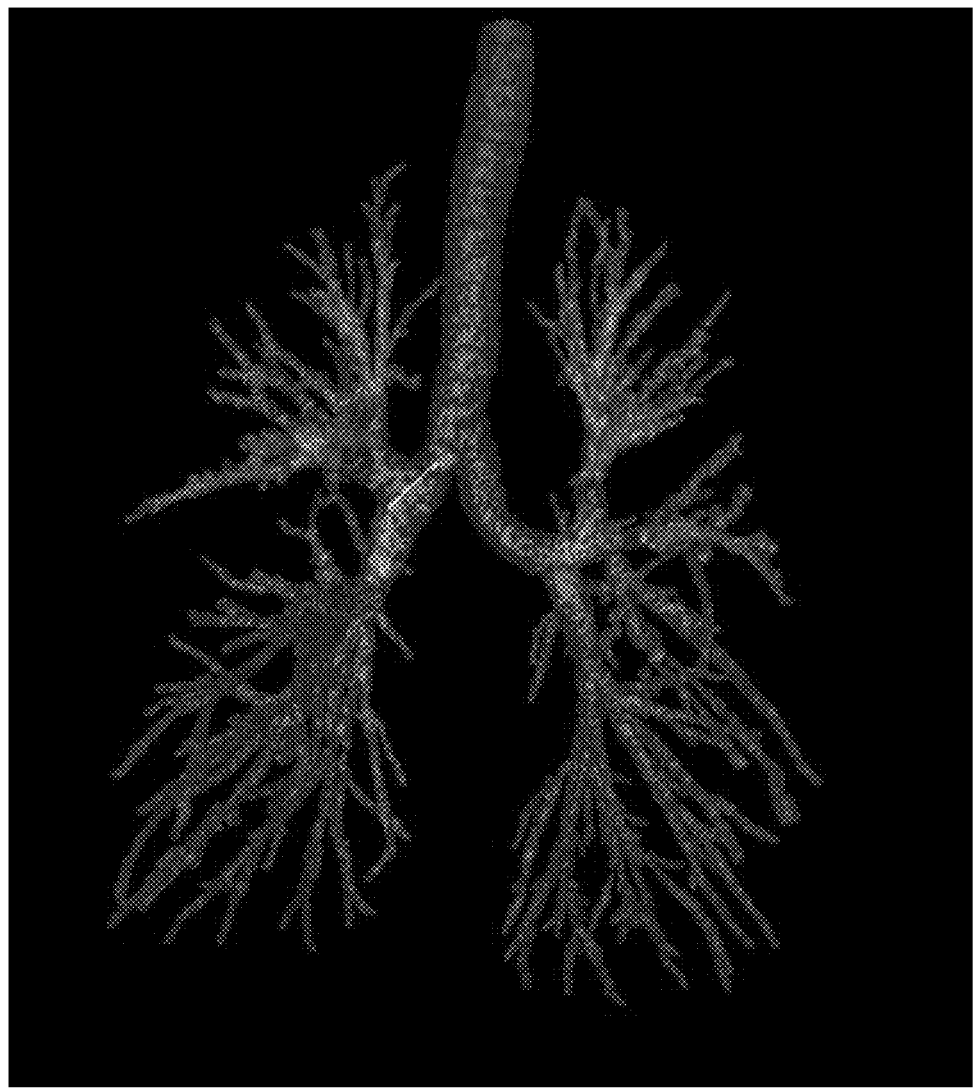
FIGURE 2C Right main bronchus

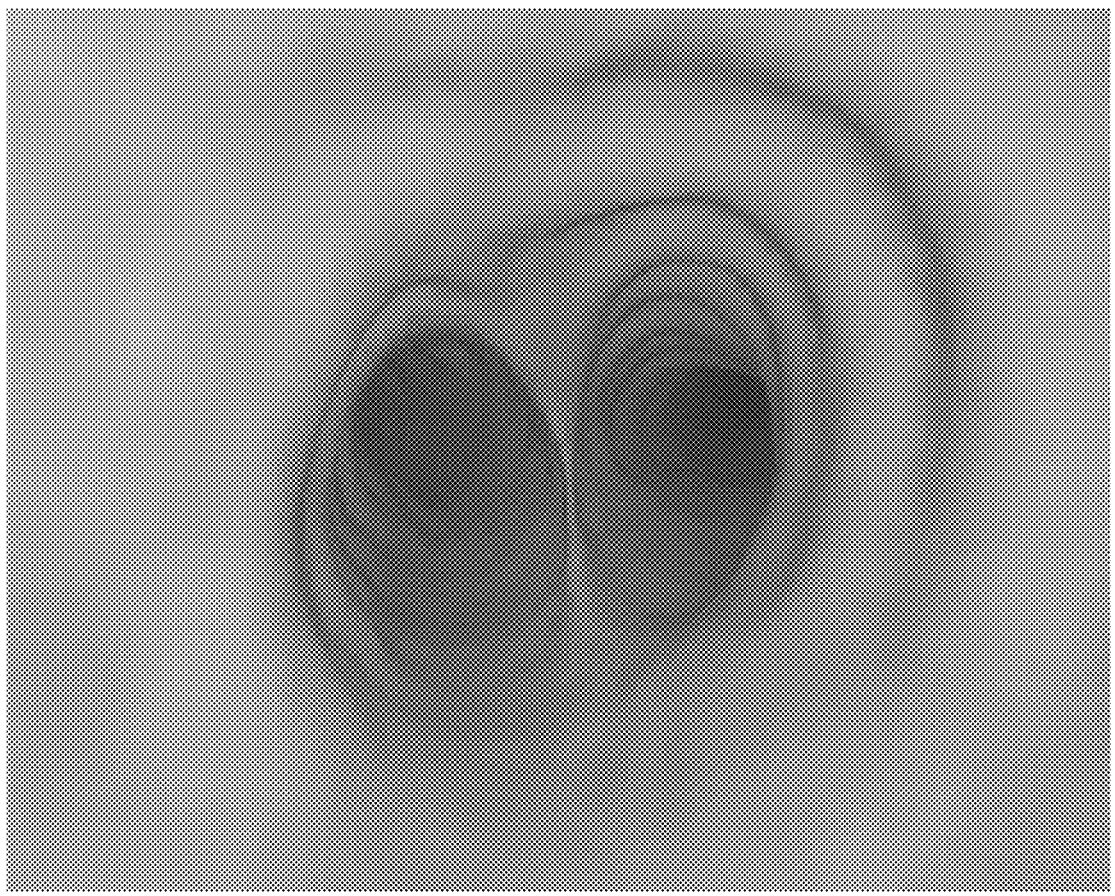
FIGURE 2D Trachea

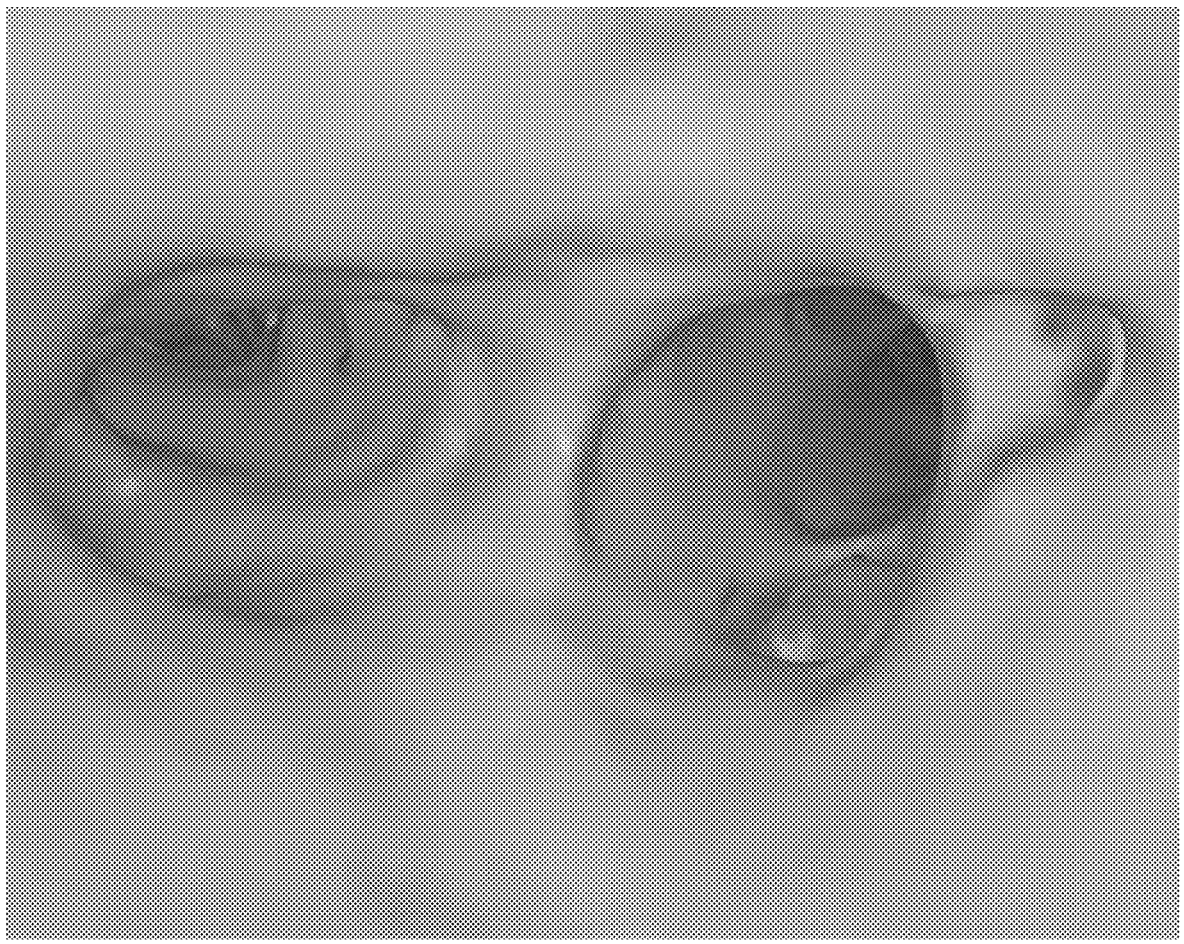
FIGURE 2E Left main bronchus

FIGURE 2F Right main bronchus

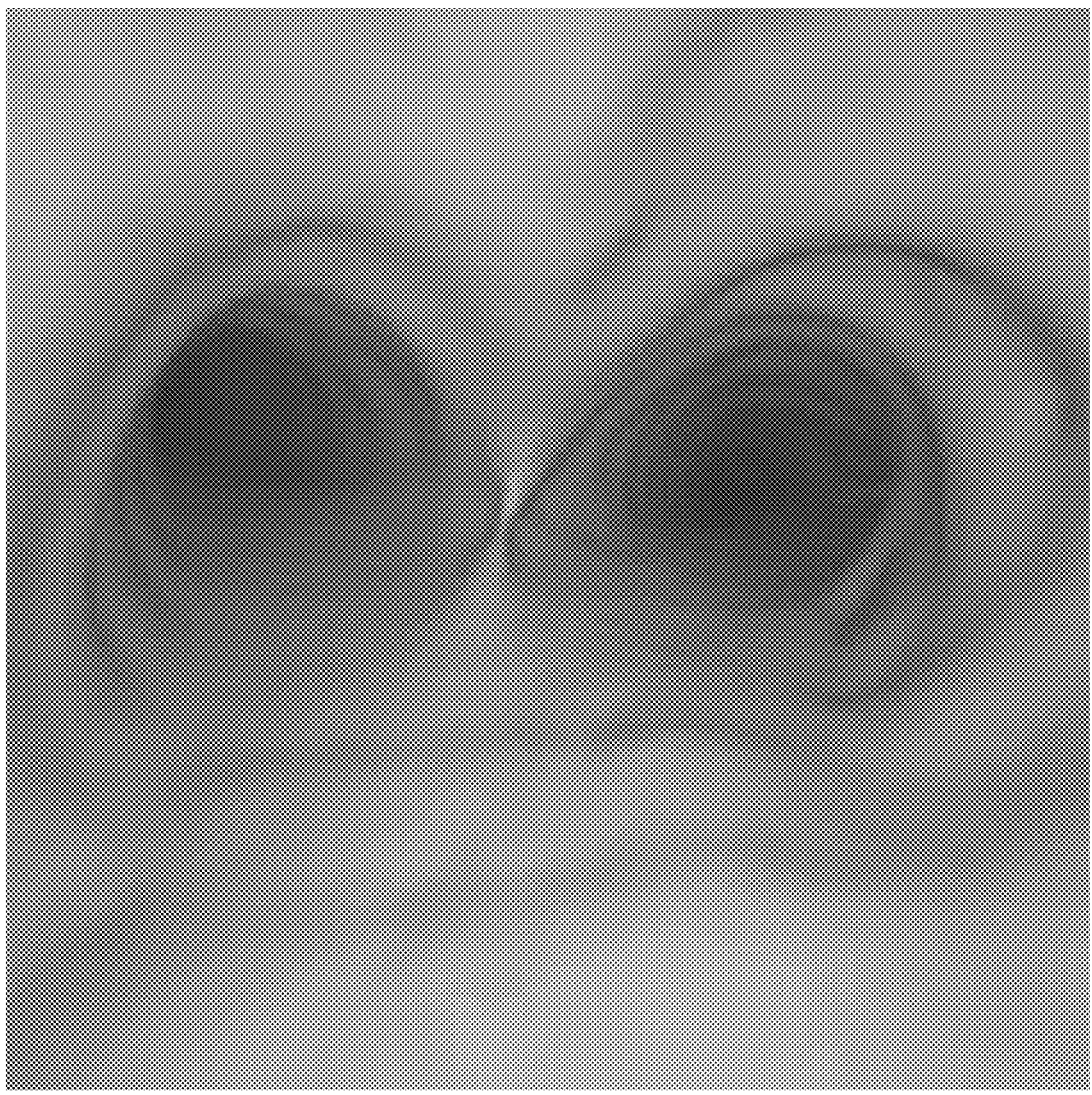
FIGURE 4B. Branch 0

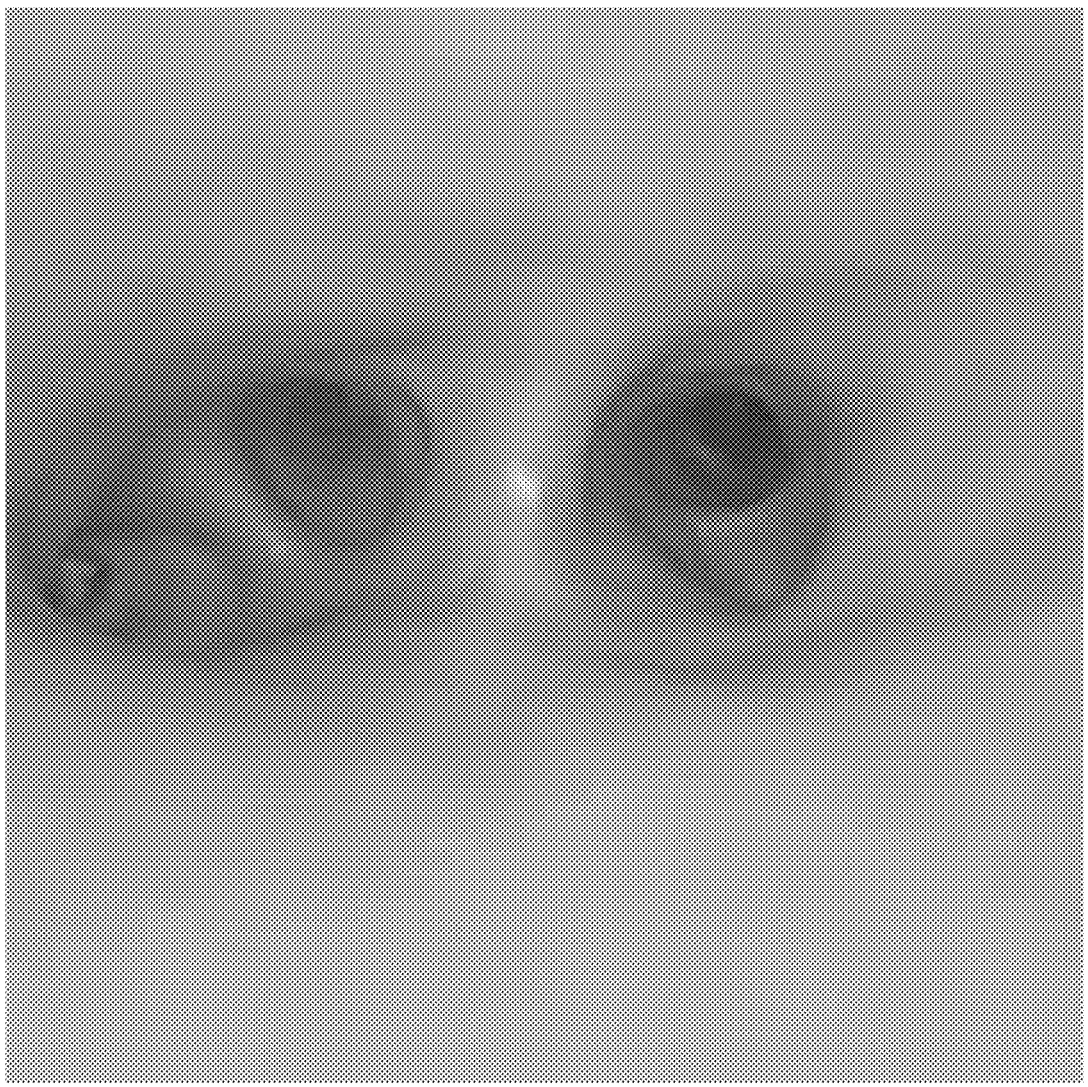
FIGURE 4C. Branch 1

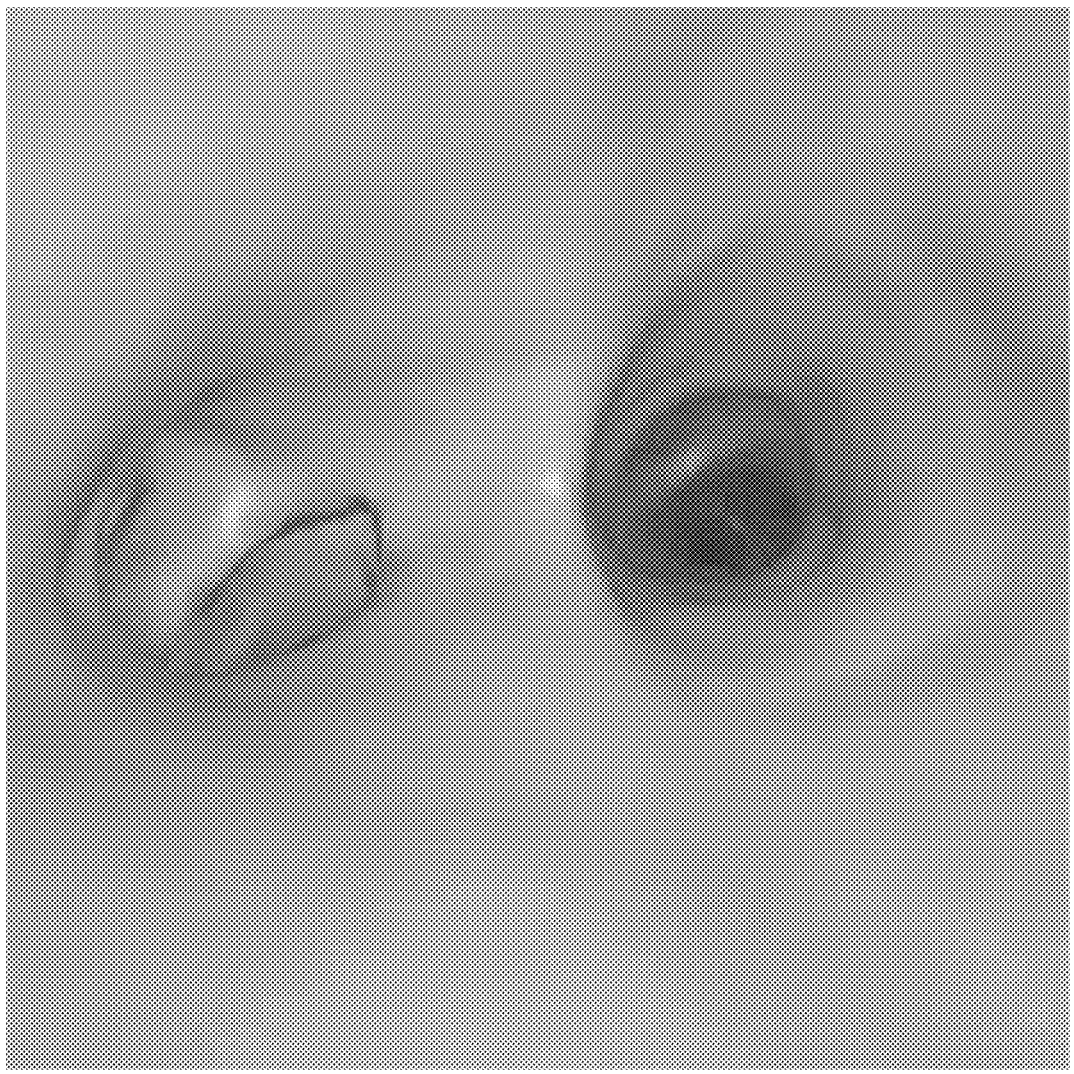
FIGURE 4D. Branch 2

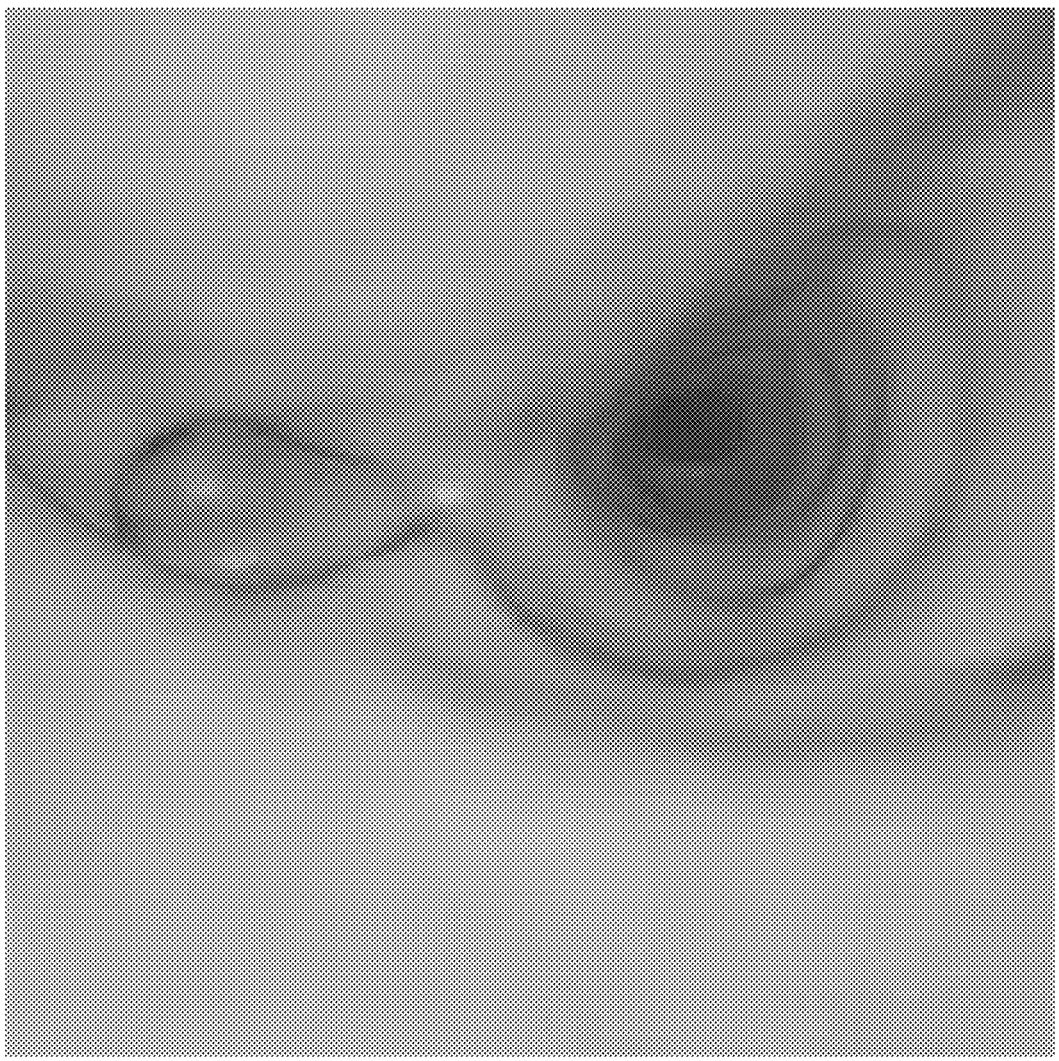
FIGURE 4E. Branch 3

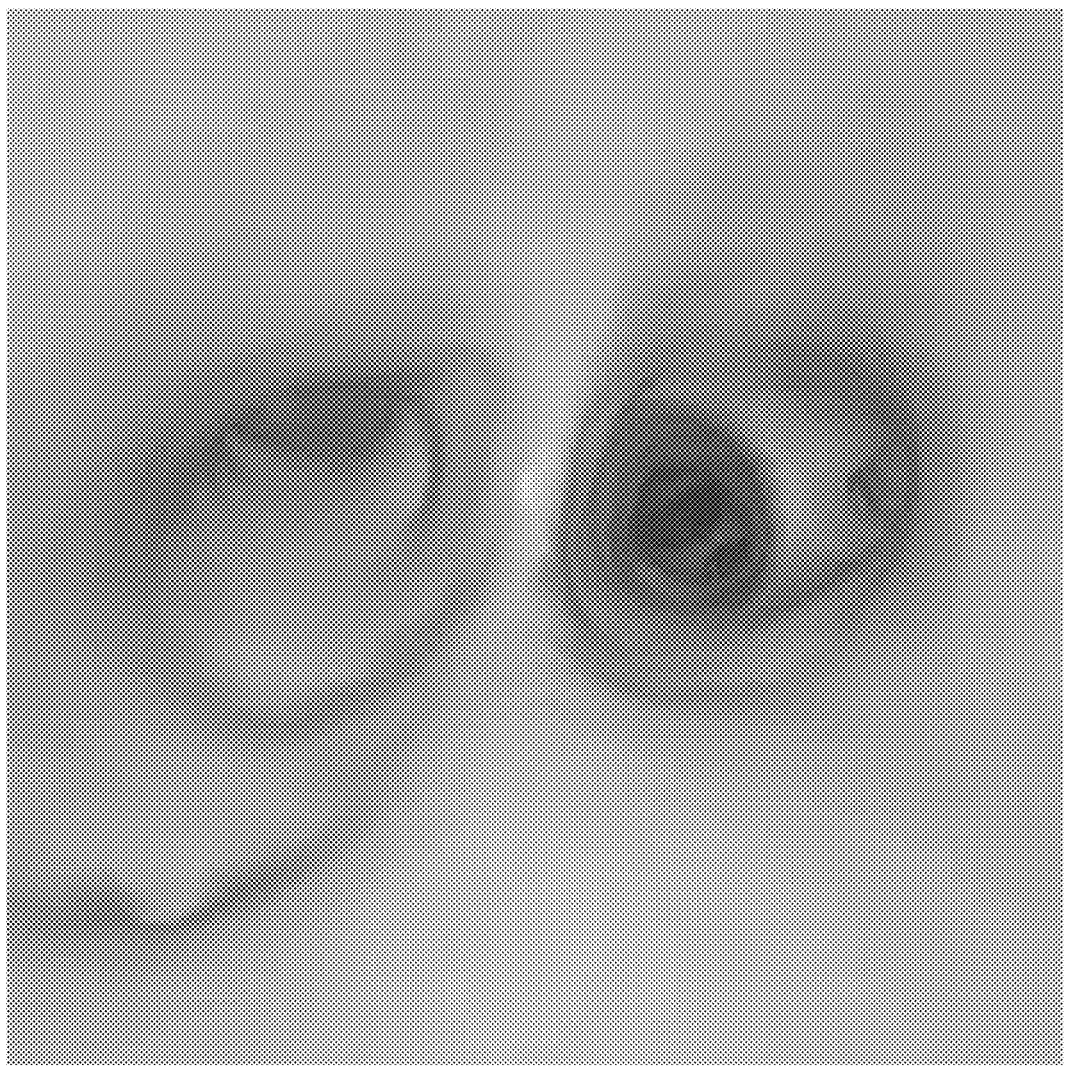
FIGURE 4F. Branch 4

FIGURE 5F $I_{CT}^{\hat{\theta}}$ for Frame 1

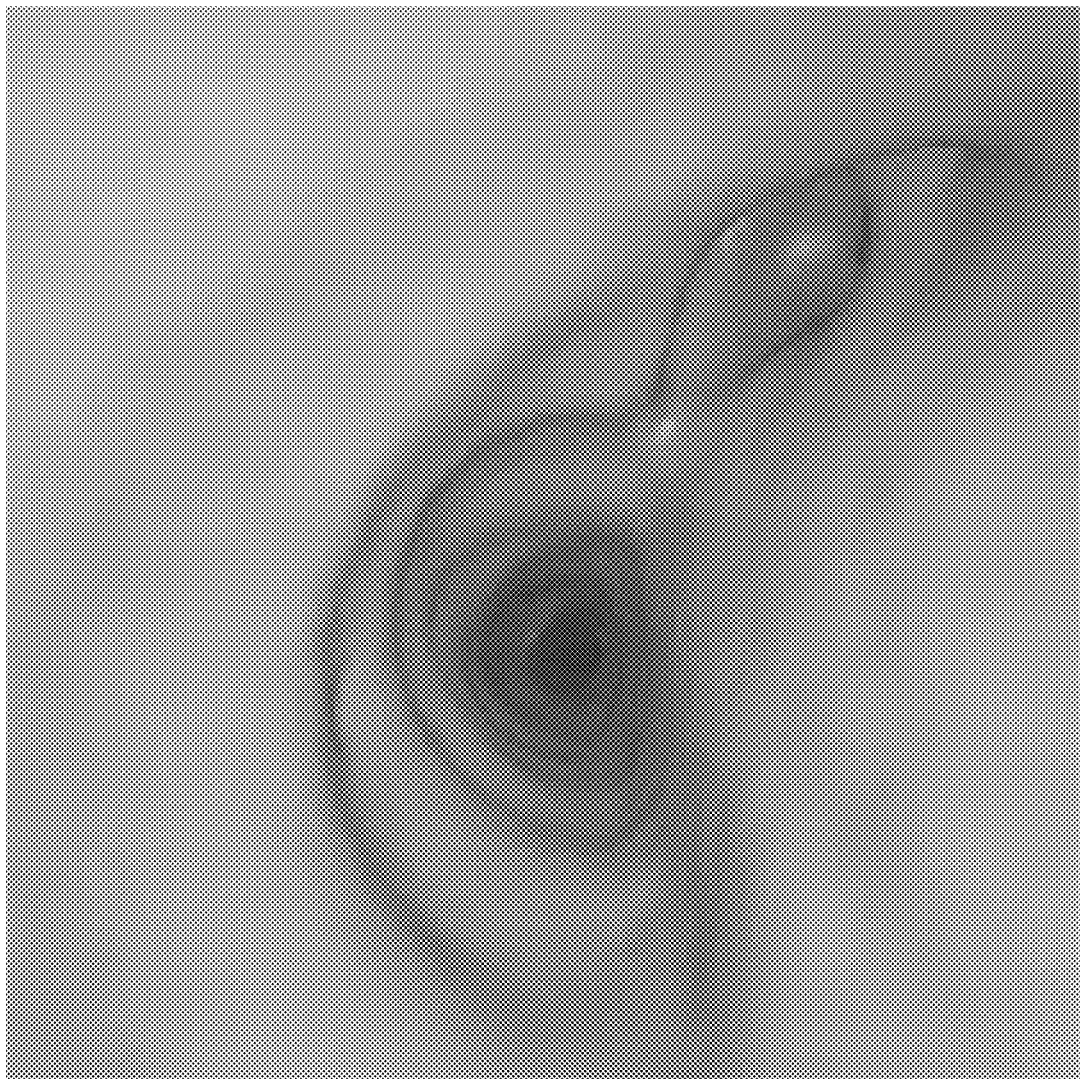
FIGURE 5G $I_{CT}^{\hat{\theta}}$ for Frame 2

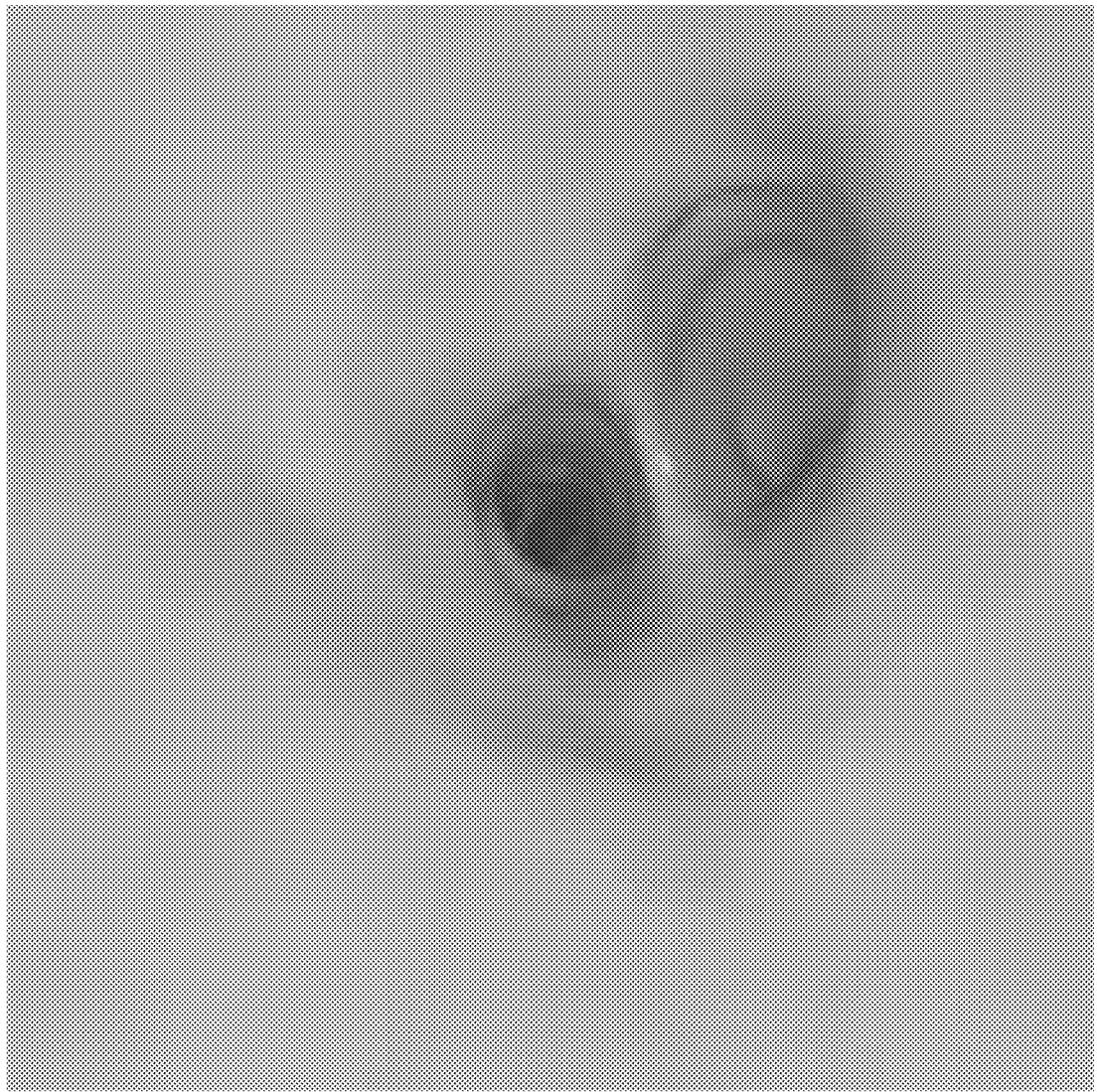
FIGURE 5H $I_{CT}^{\hat{\theta}}$ for Frame 3

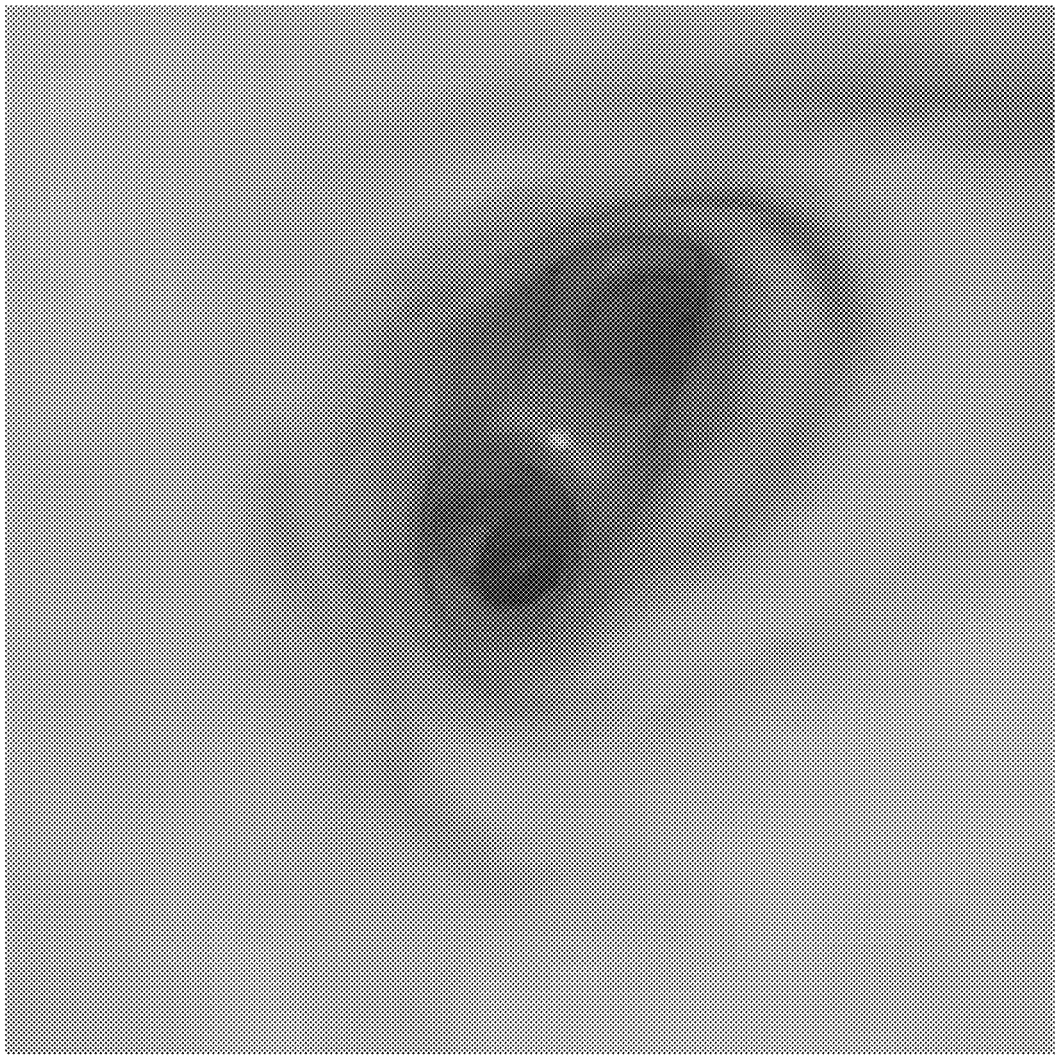
FIGURE 5I $I^{\dot{\theta}}_{CT}$ for Frame 4

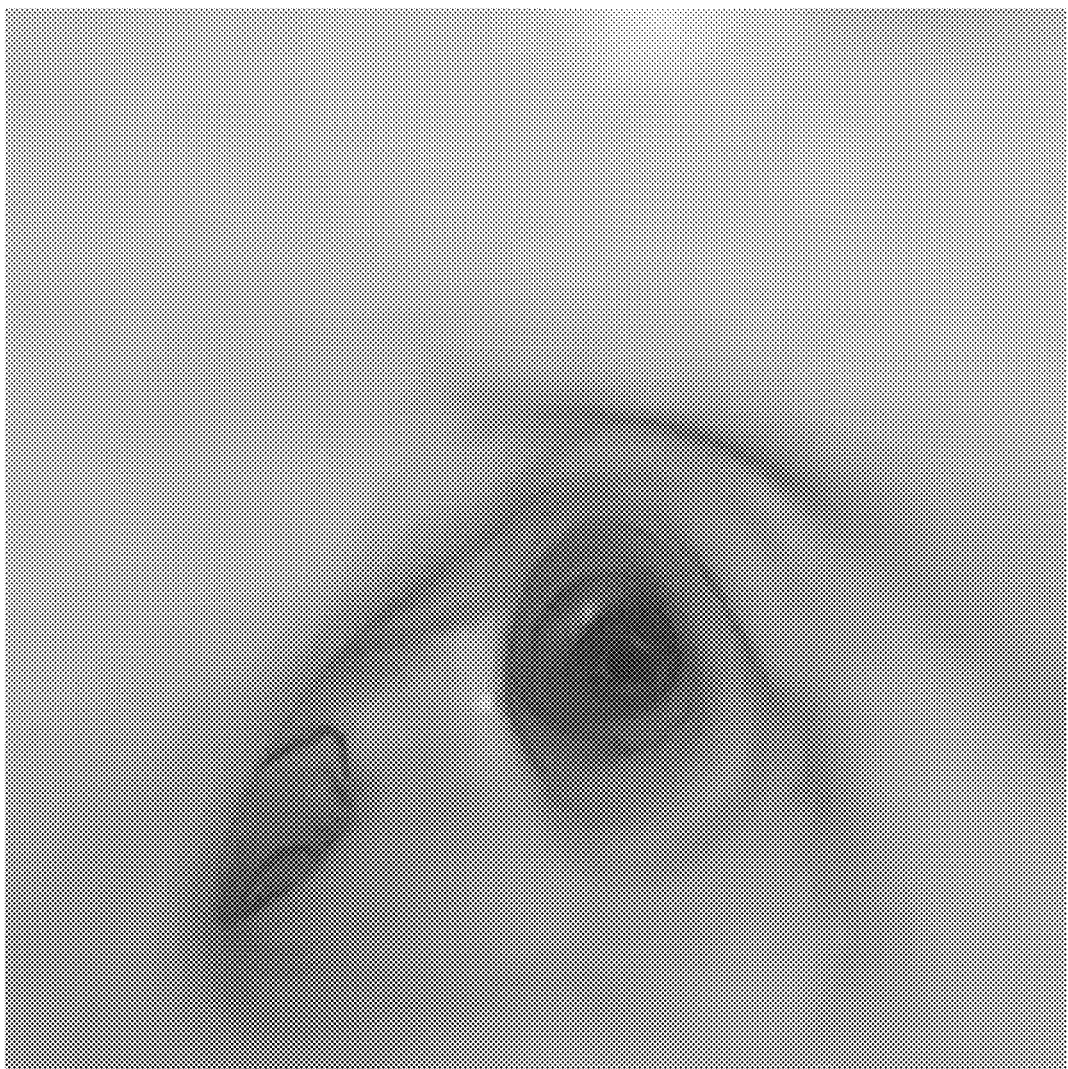
FIGURE 5J $I_{CT}^{\hat{\theta}}$ for Frame 5

IMAGE-BASED GLOBAL REGISTRATION SYSTEM AND METHOD APPLICABLE TO BRONCHOSCOPY GUIDANCE

REFERENCE TO RELATED APPLICATIONS

This application claims priority from U.S. application Ser. No. 13/016,093, filed on Jan. 28, 2011, which claims priority from U.S. Provisional Patent Application Ser. Nos. 61/299,194, filed Jan. 28, 2010 and 61/300,969, filed Feb. 3, 2010, the entire content of which being incorporated herein by reference.

GOVERNMENT SUPPORT

This invention was made with government support under Grant Nos. CA074325 and CA091534 awarded by the National Institutes of Health. The government has certain rights in the invention.

FIELD OF THE INVENTION

This invention relates generally to bronchoscopy and, in particular, to a global registration system and method useful in image-based bronchoscopy guidance systems and other applications, including other types of endoscopic procedures.

BACKGROUND OF THE INVENTION

Bronchoscopy is a medical procedure commonly used in lung-cancer assessment[1]. Lung-cancer assessment involve two main stages[2, 3, 4]: 1) three-dimensional (3D) multi-detector computed-tomography (MDCT) image assessment; and 2) live bronchoscopy. During MDCT assessment, the physician uses the two-dimensional (2D) transverse slices obtained from the patient's MDCT scan to identify specific diagnostic regions of interest (ROIs), such as lymph nodes and suspicious nodules[5, 6, 7]. In this step, the physician also identifies the closest route to each ROI and mentally plans a 3D route using the 2D slices. During bronchoscopy, the physician maneuvers a flexible bronchoscope through the lung airways towards each ROI along the pre-planned mentally defined route. This is done by identifying the bifurcations along the route on the live endoluminal video feed obtained from the bronchoscope. This manually-based route planning procedure proves to be challenging, resulting in errors in bronchoscopy as early as the second airway generation[8, 9].

Image-guided bronchoscopy guidance systems enable more accurate bronchoscopy [4, 10, 11, 12, 13]. These systems are motivated by virtual bronchoscopy (VB), wherein the 3D MDCT image of a person's chest serves as a "virtual environment"[14, 15, 16]. A software-defined virtual camera navigates through the lungs in the virtual environment and presents endoluminal renderings of the 3D data, also known as VB images. To facilitate guidance during bronchoscopy, all bronchoscopy guidance systems rely on some method for registration of the real bronchoscope in 3D surgical space to the 3D MDCT virtual space. Based on the type of sensor used for registration, bronchoscopy guidance systems can be either electromagnetic (EM) or image-based[3, 4, 11, 12, 13, 15, 16, 17, 18].

An EM-based guidance system consists of the following: 1) an EM field generator; 2) a steerable EM probe; and 3) guidance software[12, 13, 17]. The EM field generator generates an EM field around the patient's chest. The steerable EM probe is inserted through the working channel of the bronchoscope and tracked in the external EM field. Prior to the start of bronchoscopy, the steerable probe is used to calibrate and synchronize the coordinate system of the external EM field and the MDCT coordinate system. Thus, as the EM probe is tracked during bronchoscopy, its position in the MDCT coordinate system becomes nominally known. Such a system allows for immediate establishment of the global position of the bronchoscope tip within the 3D MDCT coordinate system. However, metallic objects in the vicinity induce ferromagnetic device interference, leading to distortions in the external EM field[19]. Moreover, the patient's breathing causes chest movement that leads to registration errors[20]. These errors are magnified in the peripheral airways, as the airway branches become smaller and move with the patient's breathing. Furthermore, once the bronchoscope is guided to the ROI, the steerable probe has to be retracted from the working channel of the bronchoscope so that the biopsy tools can be inserted to collect ROI tissue samples. Thus, EM-based bronchoscopy guidance systems implicitly provide global registration, but suffer in local registration. There has been ongoing research to combine the EM and image-based guidance methods in an attempt to mitigate these problems [21, 22].

Image-based bronchoscopy guidance systems rely on volume-rendered[16, 23] or surface-rendered[3, 4, 24, 25] endoluminal images of the airway tree from the 3D MDCT scans in order to establish the location of the bronchoscope. This is generally done by comparing the VB images with the real bronchoscopic (RB) video frames. Weighted normalized sum of square difference errors (WNSSD)[24] and normalized mutual information (NMI)[3, 4, 26] are metrics that are used for comparing the images obtained from the two sources. Registration is carried out using Powell's optimization, simplex or gradient methods. The image-based bronchoscopy guidance methods rely on local registrations at bifurcations and so are less susceptible to patient breathing motion. However, as these methods rely on the bronchoscope video, they are affected by artifacts in bronchoscope video caused by patient coughing or mucous obstruction. Also, most of the available systems rely on manual registration for initialization of the bronchoscope position. During a live bronchoscopic procedure, the absence of a global registration algorithm leads to increased procedure time and some uncertainty in the bronchoscope position. This in turn leads to guidance errors. Thus, image-based bronchoscopy guidance methods implicitly provide excellent local registration, but no global registration.

Global registration is used in various fields such as image fusion[27, 28], remote sensing[29, 30], object recognition [31], and robotic navigation[32]. The problem of establishing the global position in robotic navigation is most similar to global registration in the domain of image-based computer-guided bronchoscopy. In robotic navigation, global registration is also referred to as the "robot kidnapping problem," wherein the position of a robot has to be estimated when it is moved to any arbitrary pose and no motion estimates are available[32]. Moreno et al. presented a non-linear filter, termed evolutive localization filter, that uses raw sensor data and recursively estimates the current pose[32]. Other methods utilizing multi-hypothesis Kalman filters[33, 34], grid-based probabilistic filters[35] and Monte-Carlo localization[36] methods have also been used for addressing the problem of global registration in robot navigation.

In the domain of medical imaging, global registration has been primarily used for multi-modal registration. Zhang et al. have described an adaptive region-intensity-based ultrasound and computed tomography registration[37]. Munim et al. used vector distance functions for registering magnetic resonance (MR) images of multiple patients[38]. Moghari et al. have described a global registration method for aligning multiple bone fractures to a statistical anatomical atlas model[39]. Principal component analysis and the unscented Kalman filter were used for local and global registration, respectively. Fookes et al. have also described a method for registration of multiple MR images from the same patient by formulating the problem as the minimization of a covariance weighted non-linear least square function[40].

In image-based bronchoscopy guidance, researchers have focused on the problem of local registration. However, few have worked on the problem of global registration, whereby the branch location of the bronchoscope is established. Bricault et al. have proposed a multi-level strategy for registration[23]. In this work, the relative position change of the sub-division wall from one bifurcation to the next was used to identify the branch position of the bronchoscope. Shinohara et al. described a branch identification method using eigenspace-image matching[41]. However, this method addresses bronchoscope tracking and cannot be used for global registration. Moreover, it requires manual initialization.

SUMMARY OF THE INVENTION

This invention resides in a global registration system and method useful in image-based bronchoscopy guidance systems and other applications, including other types of endoscopic procedures. Synchronization is restored by identifying the current branch position, thereby facilitating global, technician-independent bronchoscopy guidance without the need for any external device such as an electromagnetic sensor.

Virtual bronchoscopy (VB) renderings of a 3D airway tree are obtained, these including VB views of branch positions within the airway tree. At least one real bronchoscopic (RB) video frame is received from a bronchoscope inserted into the airway tree. An algorithm according to the invention is executed on a computer to identify the several most likely branch positions having a VB view closest to the received RB view, and the 3D position of the bronchoscope within the airway tree is determined in accordance with the branch position identified in the VB view.

The algorithm may use various techniques to speed operation, including an intra-branch search followed by an inter-branch search. In particular, a fast search may be carried out over all the branches in a global airway-bifurcation search space, with a weighted normalized sum of squares distance metric being used to determine the best match. In a preferred embodiment the intra-branch search uses pre-computed lumen region enclosing rectangles in conjunction with a fast local registration refinement.

The intra-branch search is given by:

$$\hat{\theta}^{b_i} = \underset{\chi \in b_i}{\operatorname{argmax}} C(I_V, I_{CT}^{\chi})$$

where $C(\cdot,\cdot)$ is a similarity function, $\hat{\theta}^{b_i}$ is the optimum view point in branch i for the given RB video frame $I_V$ and $b_i$ is a subset of $K_{tree}$ and contains all the view points in branch I.

The inter-branch search is given by:

$$\hat{\theta}^o = \arg\underset{\chi \in K_{\hat{\theta}^{b_i}}}{\min} D(I_V, I_{CT}^{\chi})$$

where $K_{\hat{\theta}^{b_i}} = \{\hat{\theta}^{b_1}, \hat{\theta}^{b_2}, \ldots, \hat{\theta}^{b_n}\}$ is the set of view points obtained from the intra-branch search.

Results show that the algorithm currently needs 3 seconds per search-space branch, with a trend of improving accuracy with reducing search-space being seen. The algorithm gives accuracy rates ≈90% when using multiple views of the same bifurcation. When using the airway phantom, where a lighting model of the test frames was different from that used for the VB frames, a global registration accuracy of 89% was obtained.

BRIEF DESCRIPTION OF THE DRAWINGS

FIGS. 2A-2F show examples of the 3D airway tree and the virtual bronchoscope;

FIGS. 4B-4F show the VB images associated with the best bronchoscope position as found by the intra-branch search in five different branches of the search space;

FIGS. 5F-5J show VB images at the bronchoscope position estimated by the algorithm for airway phantom.

DETAILED DESCRIPTION OF THE INVENTION

During bronchoscopy, the physician maneuvers a bronchoscope through the airway tree. An image-based bronchoscopy guidance system provides discrete guidance at bifurcations. In order to register the view seen in the bronchoscope video with multi-detector computed-tomography MDCT co-ordinate system, we model the image seen by the bronchoscope by using 3D MDCT data.

Figure 1A:
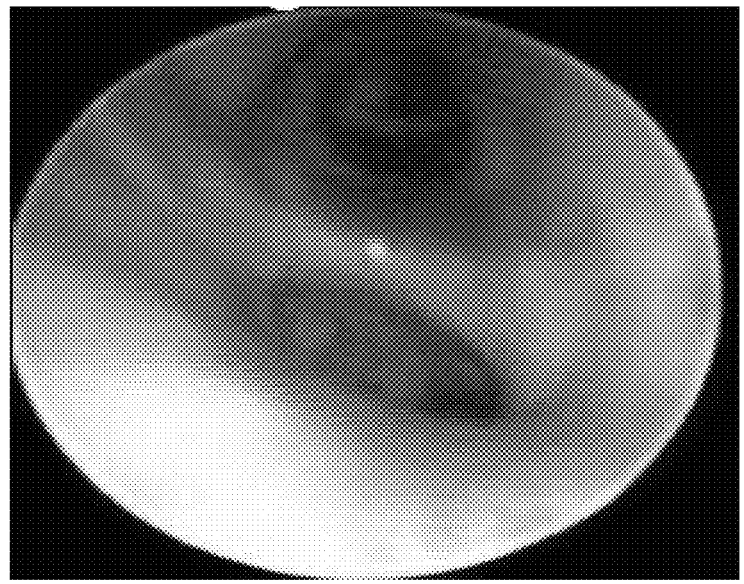
FIGS. 1A and 1B show bronchoscopic video frame distortion correction.
Figure 1B:

To model the VB views, the bronchoscope camera is first calibrated by using an off-line procedure [42]. Parameters such as the focal length f and the FOV angle of the camera are computed. Coefficients are also found in order to correct the barrel distortion of the video frames as seen in FIG. 1. FIGS. 1A and 1B show bronchoscopic video frame distortion correction. In particular, FIG. 1A shows an example of a bronchoscopic video frame with barrel distortion, and FIG. 1B shows the bronchoscopic video frame after distortion correction.

To create VB views, the airway tree is automatically segmented using a robust segmentation algorithm [43]. The marching cubes algorithm is run on the 3D segmentation to obtain polygonal surface representation of the airway tree [44]. The virtual bronchoscope is designed as a pinhole camera model with a focal length of f and the same image dimensions as the bronchoscope camera. The endoluminal airway surfaces are assumed to be Lambertian, with the light source at the focal point. Secondary reflections are disregarded. Using these assumptions, the VB view is rendered using OpenGL[45] as shown in FIGS. 2A-2F. Virtual bronchoscopic views. FIGS. 2A-2C show examples of the 3D airway tree and the virtual bronchoscope (yellow cylinder+ graphical needle) positioned within the trachea, left main bronchus and the right main bronchus (shown in FIGS. 2D-2F) and the corresponding VB views.

The Global Registration Problem

Global registration can be defined as establishing the current branch position of the bronchoscope in the 3D airway tree. To formulate the global registration problem, we consider the scenario where the bronchoscope is "blindly" inserted into the airway so that it lies at some bifurcation. We denote the real bronchoscopic (RB) video frame from the bronchoscope as $I_V(x, y)$. The virtual bronchoscopy (VB) renderings obtained from the virtual bronchoscope are denoted by $I_{CT}(x, y)$. The current unknown viewpoint of the bronchoscope is denoted by $\theta=(x, y, z, \alpha, \beta, \gamma)$, where $(x, y, z)$ gives the 3D spatial position and $(\alpha, \beta, \gamma)$ specifies the Euler angles. The global registration algorithm finds the branch that contains the viewpoint with a VB view closest to the given RB view.

This problem can be posed as a Maximum A Posteriori (MAP) problem. The first part is probability density estimation problem, where we estimate the posterior density over the space of available bronchoscope poses given the incoming bronchoscopic video. This problem formulation is similar to that by Moreno et al [32]. In that paper, an iterative solution is used for global registration but we present a method for registration using a single frame which is similar to the method by Wei β et al [46]. From MAP point of view, the global registration problem is an optimization problem where we estimate the branch in which the bronchoscope gives a pose that maximizes the posteriori probability density $$\hat{\theta} = \arg\max_{\chi \in K_{tree}} p(\chi | I_V) \qquad (1)$$

where $\hat{\theta}$ is the estimated optimum view point, $\chi$ is one of the view points in $K_{tree}$, the search space for the view points and $p(\chi|I_V)$ is the posterior density over the space of available bronchoscope poses given the incoming bronchoscopic video. Using Bayes theorem, we get $$p(\chi | I_V) = \frac{p(I_V | \chi) \cdot p(\chi)}{p(I_V)} \qquad (2)$$

In the above expression, if all bronchoscope poses are considered equi-likely $p(\chi)$ can be considered as a constant and $p(I_V)$ is a constant with respect to $\chi$. Thus, we get $$\arg\max p(\chi|I_V) = \arg\max p(I_V|\chi) \qquad (3)$$

The term $p(I_V|\chi)$ can be estimated using a similarity function that finds the similarity between $I_V$ and the VB image rendered at $\chi$, given by $I_{CT}^\chi$. Hence, (3) becomes $$\arg\max p(I_V|\chi) = \arg\max C(I_V, I_{CT}^\chi) \qquad (4)$$

where $C(\bullet,\bullet)$ is a similarity function that gives the measure of similarity between the bronchoscopic video frame $I_V$ and $I_{CT}^\chi$ the rendering obtained at pose $\chi$. If the similarity function $C(\bullet,\bullet)$ is replaced by a dissimilarity measure, the global registration problem becomes $$\hat{\theta} = \arg\min_{\chi \in K_{tree}} D(I_V, I_{CT}^\chi) \qquad (5)$$

here $D(\bullet,\bullet)$ is a dissimilarity function between the RB image $I_V$ and the VB view $I_{CT}^\chi$ at view point $\chi$ and $K_{tree}$ is the search space for the view points. The optimum branch is given by $$b^\circ = B(\theta) \qquad (6)$$

where $B(\bullet)$ is a function that finds the branch containing the view point $\hat{\theta}$.

The proposed algorithm accepts as input one or more live bronchoscopic video frames and outputs the 3D position of the bronchoscope within the airway tree. The algorithm is invoked during live bronchoscopy when the position of the bronchoscope is unknown. The algorithm will then determine the bronchoscope position within the airway tree. Before invoking the algorithm, the physician positions the bronchoscope to give a good view of an airway bifurcation, so that the lumen region is well represented, as shown in FIG. 4. Multiple runs of the algorithm on either the same bifurcation or at related bifurcations (parent-daughter branches) can be used to improve the overall accuracy of the method. The algorithm broadly divides into two major stages: intra-branch search and inter-branch search.

Figure 3:
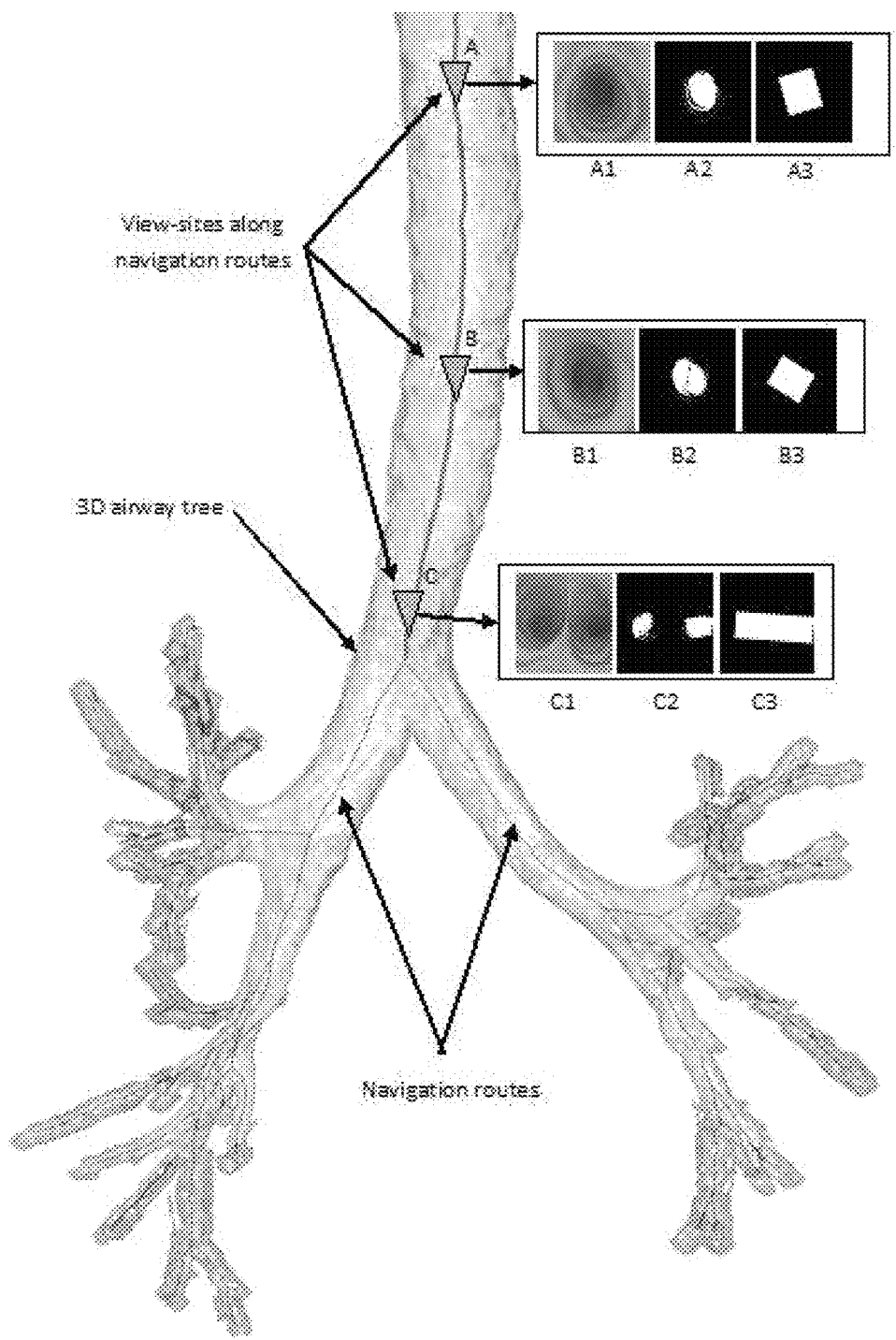
FIG. 3 illustrates a pre-computation for intra-branch search.

FIG. 3 illustrates a pre-computation for intra-branch search. This figure shows the pre-computation carried out for the branch highlighted by the blue line. The red lines are the pre-defined centerline navigation routes through the 3D airway tree. The green triangles highlight three of the pre-defined view-sites (A, B, C) along the selected branch. The figures to the right of the view-sites are the VB renderings (A1, B1, C1), the lumen thresholded images (A2, B2, C2) and the minimum enclosing rectangles (A3, B3, C3) associated with the respective view-sites. The longer length of the minimum enclosing rectangle is saved during pre-computation and later used for localizing the position of the given RB frame in a given branch.

Intra-Branch Search

The intra-branch search is formulated as $$\hat{\theta}^{b_i} = \arg\max_{\chi \in b_i} C(I_V, I_{CT}^\chi) \qquad (7)$$

where $C(\bullet,\bullet)$ is a similarity function, $\hat{\theta}^{b_i}$ is the optimum view point in branch i for the given RB video frame $I_V$ and $b_i$ is a subset of $K_{tree}$ and contains all the view points in branch i.

This optimization process needs spanning through all possible view positions in a given branch. This is not practical in a real-time algorithm due to the excessive time involved. Hence, we use a novel intra-branch search which comprises of two steps. In the first step, the intra-branch search carries out a fast scan through all the pre-defined view sites along the centreline of the branch. The second step comprises render position adjustment using fast local registration. Because of uncertainty in the roll angle of the bronchoscope we use a set of four likely positions for each branch using different roll angles.

The minimum enclosing rectangle of the lumen region has a change in its larger dimension as the render position moves along the centreline towards the bifurcation as shown in FIG. 3. This is the underlying idea of the fast-scan search along the centreline. In this search, first the input real image $I_V$ is thresholded to segment out the lumen region. The p-tile thresholding with a value of p=10 has been empirically found to give good results for segmenting out the lumen. Once the lumen region is segmented, the convex hull of the segmented region is found. We use the Bentley-Faust-Preparata (BFP) fast approximate 2D convex hull algorithm for this purpose [47]. This convex hull is used to find the minimum enclosing rectangle of the lumen region as shown in FIG. 3. The larger dimension of the enclosing rectangle is saved as $\text{Dim}_{Max}$. The same feature extraction step is carried out at all the pre-defined centreline view points of all the branches as a pre-computation step and the larger dimension of the enclosing rectangle is saved. During live global registration, the intra-branch search gives the best centreline view-point at each branch that has its feature value closest to $\text{Dim}_{Max}$. The best rendering position that is obtained has a fixed roll angle. However, the real image could have any possible roll angle. To address this, roll angles of 90 degrees, 180 degrees and 270 degrees are applied to this rendering position resulting in the four best rendering positions for each branch.

The real image is obtained from a bronchoscope having multiple degrees of freedom. So the four best rendering positions obtained in the previous step may not give rendering images $I_{CT}$ similar to the real image $I_V$. Therefore, the four rendering positions obtained from the previous step are adjusted further using the inverse compositional method for local registration [24]. The local registration uses WNSSD metric for image comparison and the optimal Gauss-Newton gradient for parameter update ($\iota_\Delta$) as given in (8) and (9).

$$D_1 = \left\{ \sum_{u,v} w_{u,v} \left[ \frac{I_{CT}(u,v) - \mu_{CT}}{\sigma_{CT}} - \frac{I_V(u,v) - \mu_V}{\sigma_V} \right]^2 \right\} \quad (8)$$

where $\mu_{CT}$ and $\mu_V$ are the respective weighted-image means and $\sigma_{CT}^2$ and $\sigma_V^2$ are the respective weighted image variances and $w_{u,v}$ are weights that can be used to arbitrarily assign higher importance to pixels in the image based on geometry, graylevel value, gradient strength, or any appropriate confidence measure. Here, we use the trivially weighted case $$w_{u,v} = 1, \forall u, v$$

$$\Theta_\Delta = H^{-1}\Big|_{\Theta=0}^\rho \sum_{u,v} w_{u,v} \left[ \frac{\partial I_{CT}}{\partial \Theta} \right]_{\Theta=0}^T \Big|_{\Theta=0}^\rho [\bar{I}_V(W(u,v,Z;\Theta_{eq})) - \bar{I}_{CT}(u,v)] \quad (9)$$

where $$\left[ \frac{\partial I_V}{\partial \Theta} \right]_\Theta$$

is a 6D row vector of steepest-descent images, $\bar{I}_V(W(u,v,Z;\Theta_{eq}))$ and $\bar{I}_{CT}(u,v)$ are the normalized images and H, the Gauss-Newton Hessian is computed as $$H = \sum_{u,v} W_{u,v} \left[ \frac{\partial I_V}{\partial \Theta} \right]^T \left[ \frac{\partial I_V}{\partial \Theta} \right] \quad (10)$$

Parameter update is run for 200 ms, which is sufficient for convergence and limits the total run-time of the algorithm resulting in four image rendering positions for each branch.

The rendered images at each of these positions are thresholded to obtain the lumen region. These thresholded images are then compared with the lumen thresholded image obtained from the real image using the metric $C_1$ described in equation (11). Substituting from equation (11) in equation (7) we get the best rendering position of the branch.

$$C_1(I_1, I_2) = \frac{n_{I_1 \cap I_2}}{n_{I_1 \cup I_2}} \quad (11)$$

where $$n_{I_1 \cap I_2} = \begin{cases} 1 & \text{if } I_1(u,v) > 0 \text{ and } I_2(u,v) > 0 \\ 0 & \text{otherwise} \end{cases}$$

and $$n_{I_1 \cup I_2} = \begin{cases} 1 & \text{if } I_1(u,v) > 0 \text{ and } I_2(u,v) > 0 \\ 0 & \text{otherwise} \end{cases}$$

Inter-Branch Search

The inter-branch search is given by $$\hat{\theta}^o = \arg\min_{\chi \in K_{\hat{\theta}_i^b}} D(I_V, I_{CT}^\chi) \quad (12)$$

where $K_{\hat{\theta}_i^b} = \{\hat{\theta}^{b_1}, \hat{\theta}^{b_2}, \ldots, \hat{\theta}^{b_n}\}$ is the set of view points obtained from the intra-branch search. In (12) we use the WNSSD dissimilarity metric as defined in equation (8). The optimum view point is used to find the current bronchoscope branch position using equation (6).

Figure 4A:
FIG. 4A shows an input RB frame.
Figure 5A:
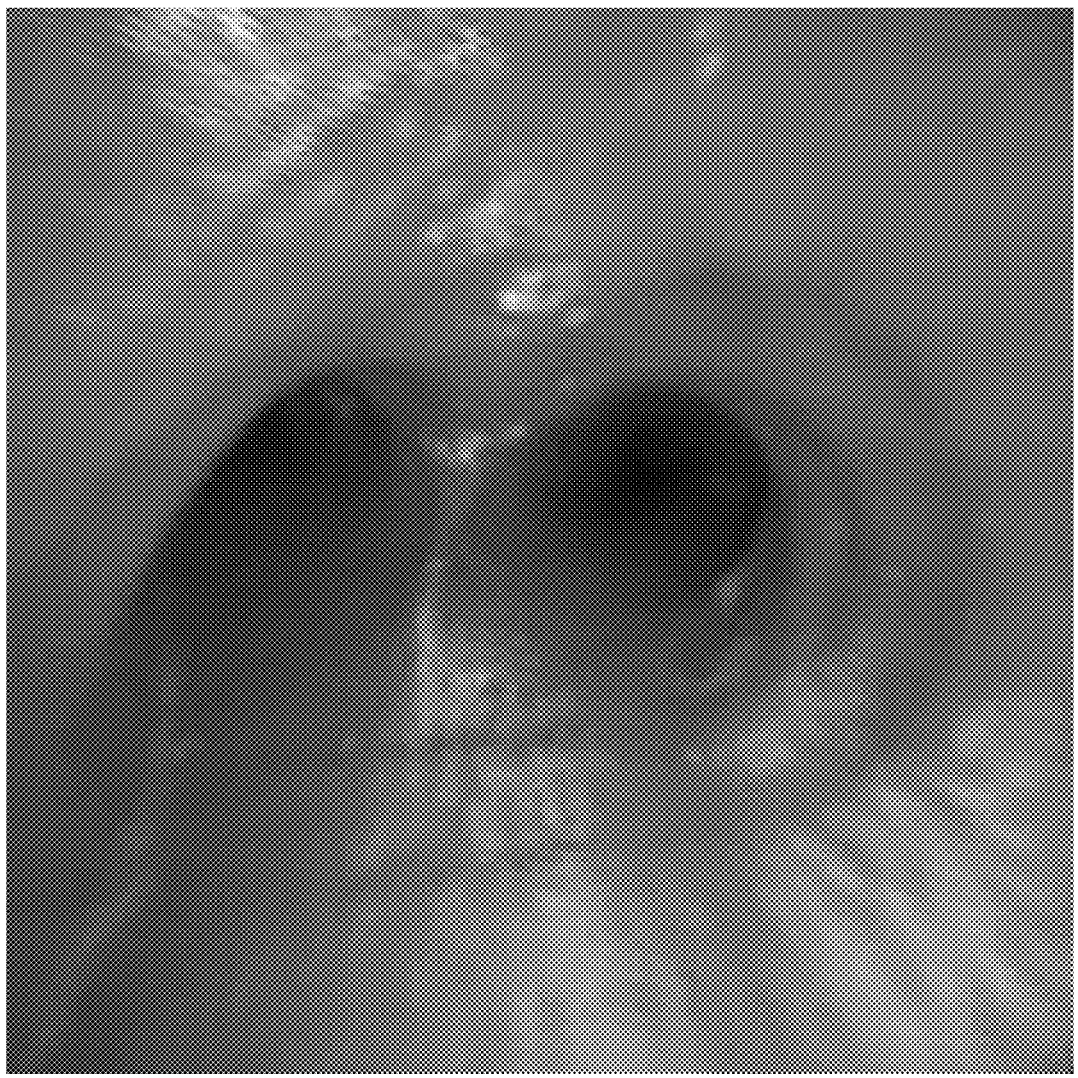
FIGS. 5A-5E show input bronchoscopic video frames for airway phantom.
Figure 5B:
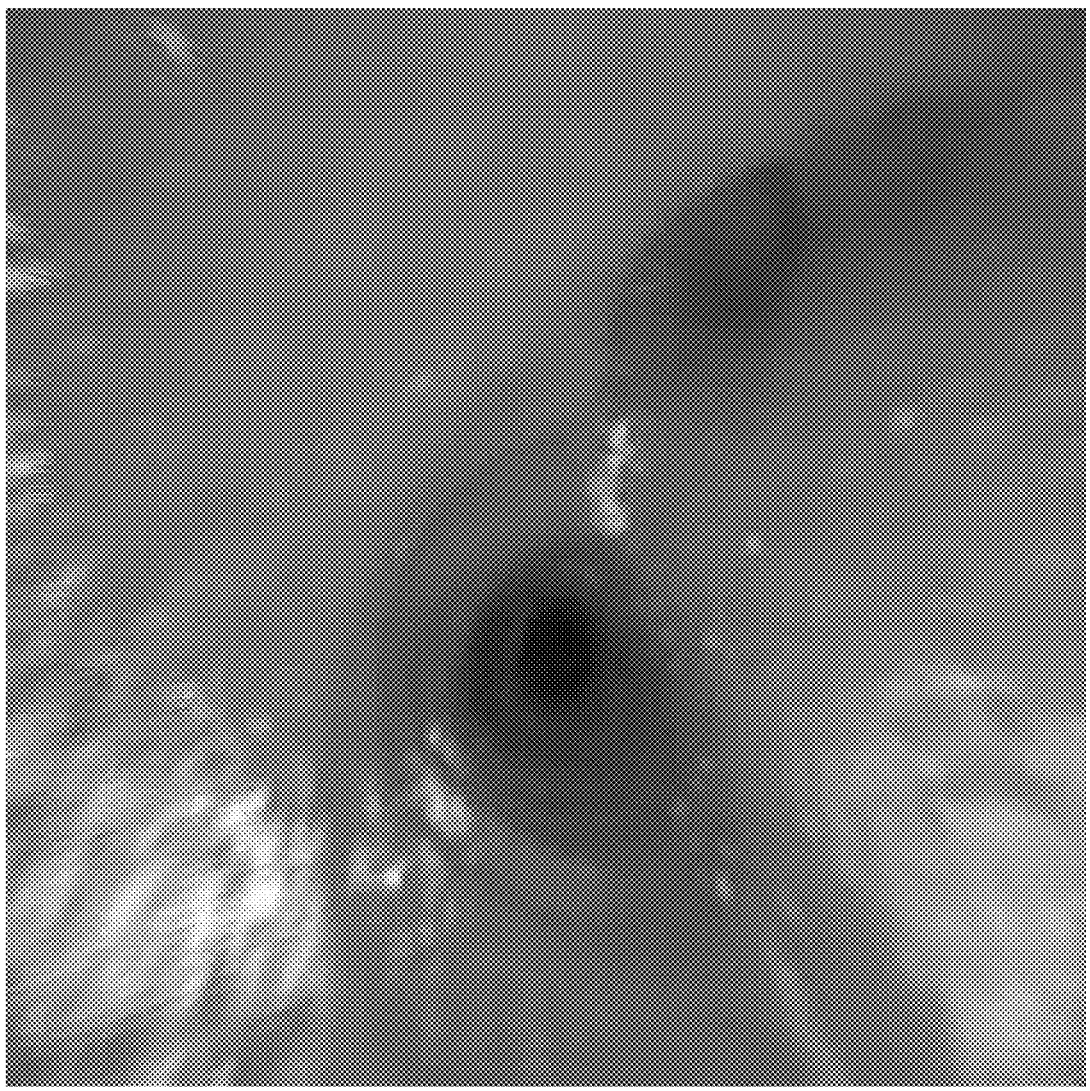
Figure 5C:
Figure 5D:
Figure 5E:

The above global registration method has been summarized in equation (12). FIGS. 4A-4F show the best matches for the different branches of the search space and FIG. 4B, the correctly identified branch after the inter-branch search. FIG. 4A shows the input RB frame and FIGS. 4B-4F show the VB images associated with the best bronchoscope position as found by the intra-branch search in five different branches of the search space. Inter-branch search correctly identified branch with rendering shown in FIG. 4B as the best branch.

---

Algorithm 1: Pre-computation Phase: Computation of the feature value for every view site along each branch.

---

Initialization: Computing features for every view-site along a branch
for ∀ branch i ∈ search-space do
    for ∀ view-site j ∈ branch i do
        Generate a virtual image $I_{CT}$.
        Threshold the image $I_{CT}$ using p-tile thresholding (p = 10).
        Use BFP algorithm to find the convex hull of the thresholded lumen region.
        Find the minimum enclosing rectangle using the convex hull.
            save the longer dimension of the rectangle by the view-site index j.
    end
end

---

Algorithm 2: Global Registration

--- for each new real image $I_V$ do
    Capture real image $I_V$ into buffer
    Threshold the real image $I_V$
    Find convex hull of the thresholded region
    Find minimum enclosing rectangle using the convex hull
    Set bestValue=∞ and bestBranch=0
    for every branch i in the search-space do -continued Algorithm 2: Global Registration

```
    Find closest branch view-site j using the pre-computed features for
branch i
    From view-site j, obtain 4 viewing positions ( roll angles of
θ = [90,180,270] ).
    Use (11) to find the VB image at the best render position for the
branch I_{CT}^{θbi}
    Use (8) to find D₁(i) ( I_{CT} = I_{CT}^{θbi}),
    if D₁(i) ≤ bv then
        bestValue = D₁(i)
        bestBranch = i
    end
  end
end
```

Results

To evaluate the accuracy of the global registration algorithm, we carried out three sets of tests. In the first set, we evaluated the global registration algorithm using virtual case studies. The second set of tests evaluated the accuracy of the global registration algorithm using RB frames obtained from the bronchoscopic exploration of an airway phantom. In the third set, we evaluated the improvement in the accuracy of the algorithm when multiple test frames were used.

Evaluation Using Virtual Cases

The global registration algorithm was evaluated using the three virtual cases derived from the CT data of consented patients as described in Table I. While using virtual bronchoscopic cases, a minimum of 28 branches from the first five airway generations were used. Four different tests were carried out by varying the search-space of the algorithm. In all tests, a virtual bronchoscopic bifurcation view was randomly selected from the branch search space—this served as the unknown "live bronchoscope video" view in the test. This bifurcation view was obtained by randomly moving to any of the view sites along a branch. A random roll angle from 0-360 degrees was used and a perturbation of up to ±5 mm was applied to the virtual bronchoscopic position to move the virtual bronchoscope off the center line. In the first test set, all branches were used for the search space. In the second set, the search space was divided into two by using branches either in the left lung or right lung only. In the third set, the search space was divided into five different parts based on the lung lobar regions. In the fourth set, only branches that were daughters of the same branch were used in the search space. The results of these tests are summarized in Table II. Global registration accuracy ranged from 71% to 92%. Note that a random selection from among 28 airway branches would only give an "accuracy" of 3.6%.

TABLE I

Summary of cases used for testing.

| Case number | Scanner | $(\Delta_X, \Delta_Y)$ in mm | Total slices | Total branches |
|---|---|---|---|---|
| 20349.3.47 | Siemens Sensation 16 | (0.55, 0.55) | 517 | 227 |
| 20349.3.49 | Siemens Sensation 40 | (0.64, 0.64) | 673 | 273 |
| 20349.3.61 | Siemens Sensation 40 | (0.6, 0.6) | 588 | 219 |

TABLE II

Global registration accuracy in percent for different test sets for virtual bronchoscopic cases.

| Case number | Full-tree (set 1) | Half-tree (set 2) | Lobar (set 3) | Branch pairs (set 4) |
|---|---|---|---|---|
| 47 | 73% | 76% | 80% | 92% |
| 49 | 75% | 77% | 83% | 91% |
| 61 | 71% | 73% | 80% | 83% |

Evaluation Using a Phantom Case

The airway phantom test involved live bronchoscopy on a preconstructed airway-tree phantom [25]. The phantom consists of 5 different accessible branch bifurcations when using a 5.9 mm diameter bronchoscope. While carrying out the global registration, each incoming video frame from the bronchoscope was used as input and the output of the global-registration algorithm was one of the five branches from the search space. In order to carry out the tests, the bronchoscope was moved to each of the five different branches and the video collected from this bronchoscope maneuver was used in the testing. From the collected video, only those frames that gave good bifurcation views were used in the study. A total of 836 such frames were obtained. The global registration algorithm gave an accuracy of 89% for the 836 frames (see FIG. 5A-5J). FIGS. 5A-5J show global registration results for airway phantom. The top row (FIGS. 5A-5E) are the input bronchoscopic video frames and the bottom row (FIGS. 5F-5J) are the VB images at the bronchoscope position estimated by the algorithm.

Evaluation Using Multiple Frames

To evaluate the performance of the global registration algorithm using multiple frames, the virtual cases described in Table I were used. This test setup was the same as that used for evaluation using virtual cases. We carried out two sets of tests. In the first set, multiple "random views" of the same bifurcation were used for testing. In this testing methodology, each of the frames was independently evaluated by the global registration algorithm. The frame that gave the lowest WNSSD metric (bestValue from (12)) decided the branch location for the frames. In the second set, test frames from two consecutive bifurcations were used. Both the branches were independently evaluated. Of the two test frames, the frame giving the lower WNSSD metric determined the branch pair. The results for this set of testing has been summarized in Table III. The global registration accuracy ranges from 82% to 99%. In all of the above tests, the algorithm was found to run in an average time of 2-3 seconds per search space branch.

TABLE III

Global registration accuracy in percent when using multiple test frames for virtual bronchoscopic cases.

| Case number | 3 frame (set 1) | 5 frame (set 1) | Two consecutive bifurcations (set 2) |
|---|---|---|---|
| 47 | 94% | 98% | 89% |
| 49 | 95% | 99% | 87% |
| 61 | 85% | 86% | 82% |

REFERENCES

1. K. P. Wang, A. C. Mehta, and J. F. Turner, eds., *Flexible Bronchoscopy*, 2nd. Ed., Blackwell Science, Cambridge, Mass., 2003.

2. A. D. Sihoe and A. P. Yim, "Lung cancer staging," *J. Surgical Research*, vol. 117, no. 1, pp. 92-106, March 2004.
3. J. P. Helferty, A. J. Sherbondy, A. P. Kiraly, and W. E. Higgins, "Computer-based system for the virtual-endoscopic guidance of bronchoscopy," *Comput. Vis. Image Underst.*, vol. 108, no. 1-2, pp. 171-187, October-November 2007.
4. W. E. Higgins, J. P. Helferty, K. Lu, S. A. Merritt, L. Rai, and K. C. Yu, "3D CT-video fusion for image-guided bronchoscopy," *Comput. Med. Imaging Graph.*, vol. 32, no. 3, pp. 159-173, April 2008.
5. E. A. Kazerooni, "High resolution CT of the lungs," *Am. J. Roentgenology*, vol. 177, no. 3, pp. 501-519, September 2001.
6. N. C. Dalrymple, S. R. Prasad, M. W. Freckleton, and K. N. Chintapalli, "Introduction to the language of three-dimensional imaging with multidetector CT," *Radiographics*, vol. 25, no. 5, pp. 1409-1428, September-October 2005.
7. J. Ueno, T. Murase, K. Yoneda, T. Tsujikawa, S. Sakiyama, and K. Kondoh, "Three-dimensional imaging of thoracic diseases with multi-detector row CT," *J. Med. Invest.*, vol. 51, no. 3-4, pp. 163-170, August 2004.
8. D. Osborne, P. Vock, J. Godwin, and P. Silverman, "CT identification of bronchopulmonary segments: 50 normal subjects," *AJR*, vol. 142, no. 1, pp. 47-52, January 1984.
9. M. Y. Dolina, D. C. Cornish, S. A. Merritt, L. Rai, R. Mahraj, W. E. Higgins, and R. Bascom, "Interbronchoscopist variability in endobronchial path selection: a simulation study," *Chest*, vol. 133, no. 4, pp. 897-905, April 2008.
10. F. Asano, Y. Matsuno, A. Tsuzuku, M. Anzai, N. Shinagawa, H. Moriya, et al., "Diagnosis of peripheral pulmonary lesions using a bronchoscope insertion guidance system combined with endobronchial ultrasonography with a guide sheath," *Lung Cancer*, vol. 60, no. 3, pp. 366-373, June 2008.
11. S. B. Solomon, P. White, Jr., C. M. Wiener, J. B. Orens, and K. P. Wang, "Three-dimensionsal CT-guided bronchoscopy with a real-time electromagnetic position sensor: a comparison of two image registration methods," *Chest*, vol. 118, no. 6, pp. 1783-1787, December 2000.
12. T. R. Gildea, P. J. Mazzone, D. Karnak, M. Meziane, and A. C. Mehta, "Electromagnetic navigation diagnostic bronchoscopy: a prospective study," *Am. J. Resp. Crit. Care Med.*, vol. 174, no. 9, pp. 982-989, 1 Nov. 2006.
13. Y. Schwarz, J. Greif, H. D. Becker, A. Ernst, and A. Mehta, "Real-time electromagnetic navigation bronchoscopy to peripheral lung lesions using overlaid CT images: the first human study," *Chest*, vol. 129, no. 4, pp. 988-994, April 2006.
14. W. E. Higgins, K. Ramaswamy, R. Swift, G. McLennan, and E. A. Hoffman, "Virtual bronchoscopy for 3D pulmonary image assessment: State of the art and future needs," *Radiographics*, vol. 18, no. 3, pp. 761-778, May-June 1998.
15. H. P. McAdams, P. C. Goodman, and P. Kussin, "Virtual bronchoscopy for directing transbronchial needle aspiration of hilar and mediastinal lymph nodes: a pilot study," *Am. J. Roentgenology*, vol. 170, no. 5, pp. 1361-1364, May 1998.
16. K. Hopper, T. Lucas, K. Gleeson, J. Stauffer, R. Bascom, D. Mauger, and R. Mahraj, "Transbronchial biopsy with virtual CT bronchoscopy and nodal highlighting," *Radiology*, vol. 221, no. 2, pp. 531-536, November 2001.
17. H. D. Becker, F. Herth, A. Ernst, and Y. Schwarz, "Bronchoscopic biopsy of peripheral lung lesions under electromagnetic guidance: a pilot study," *J. Bronchology*, vol. 12, no. 1, pp. 9, January 2005.
18. N. Shinagawa, K. Yamazaki, Y. Onodera, K. Miyasaka, E. Kikuchi, H. Dosaka-Akita, and M. Nishimura, "CT-guided transbronchial biopsy using an ultrathin bronchoscope with virtual bronchoscopic navigation," *Chest*, vol. 125, no. 3, pp. 1138-1143, March 2004.
19. K. Mori, K. Ishitani, D. Deguchi, T. Kitasaka, Y. Suenaga, H. Takabatake, M. Mori, and H. Natori, "Compensation of electromagnetic tracking system using an optical tracker and its application to bronchoscopy navigation system," 2007, vol. 6509, p. 65090M, SPIE.
20. I. Wegner, J. Biederer, R. Tetzlaff, I. Wolf, and H.-P. Meinzer, "Evaluation and extension of a navigation system for bronchoscopy inside human lungs," in *SPIE Medical Imaging* 2007: *Visualization and Image-Guided Procedures*, Kevin R. Cleary and Michael I. Miga, Eds., 2007, vol. 6509, pp. 65091H1-65091H12.
21. T. D. Soper, D. R. Haynor, R. W. Glenny, and E. J. Seibel, "Validation of CT-video registration for guiding a novel ultrathin bronchoscope to peripheral lung nodules using electromagnetic tracking," in *Society of Photo-Optical Instrumentation Engineers (SPIE) Conference Series*, February 2009, vol. 7261 of *Society of Photo-Optical InstrumentationEngineers (SPIE) Conference Series*.
22. K. Mori, D. Deguchi, K. Akiyama, T. Kitasaka, C. R. Maurer, Y. Suenaga, H. Takabatake, M. Mori, and H. Natori, "Hybrid bronchoscope tracking using a magnetic tracking sensor and image registration," in *Medical Image Computing and Computer Assisted Intervention* 2005, J. Duncan and G. Gerig, Eds., 2005, vol. LNCS 3750, pp. 543-550.
23. I. Bricault, G. Ferretti, and P. Cinquin, "Registration of real and CT-derived virtual bronchoscopic images to assist transbronchial biopsy," *IEEE Transactions on Medical Imaging*, vol. 17, no. 5, pp. 703-714, October 1998.
24. S. A. Merritt, L. Rai, and W. E. Higgins, "Real-time CT-video registration for continuous endoscopic guidance," in *SPIE Medical Imaging* 2006: *Physiology, Function, and Structure from Medical Images*, A. Manduca and A. A. Amini, Eds., 2006, vol. 6143, pp. 370-384.
25. S. A. Merritt, J. D. Gibbs, K. C. Yu, V. Patel, L. Rai, D. C. Cornish, R. Bascom, and W. E. Higgins, "Real-time image-guided bronchoscopy for peripheral lung lesions: A phantom study," *Chest*, vol. 134, no. 5, pp. 1017-1026, November 2008.
26. J. P. Helferty and W. E. Higgins, "Technique for registering 3D virtual CT images to endoscopic video," *IEEE Int. Conf. Image Processing*, vol. II, pp. 893-896, Oct. 7-10, 2001.
27. E-Y Kang, I. Cohen, and G. Medioni, "A graph-based global registration for 2D mosaics," in *ICPR*, 2000, pp. 1257-1260.
28. Y. Wang and Lu-ping L. Xu, "A global optimized registration algorithm for image stitching," in *Image and Signal Processing*, 2008. CISP '08. Congress on, May 2008, vol. 3, pp. 525-529.
29. Y. Li and C. Davis, "A combined global and local approach for automated registration of high-resolution satellite images using optimum extrema points," in *Geoscience and Remote Sensing Symposium*, 2008. *IGARSS* 2008. *IEEE International*, July 2008, vol. 2, pp. II-1032-II-1035.

30. A. Wong and D. Clausi, "ARRSI: Automatic registration of remote-sensing images," *Geoscience and Remote Sensing, IEEE Transactions on*, vol. 45, no. 5, pp. 1483-1493, May 2007.
31. N. Gelfand, N. J. Mitra, L. J. Guibas, and H. Pottmann, "Robust global registration," in *SGP 2005: Third Eurographics Symposium on Geometry processing*, Matthieu Desbrun and Helmut Pottmann, Eds. 2005, pp. 197-206, Eurographics Association.
32. L. Moreno, S. Garrido, and D. Blanco, "Mobile robot global localization using an evolutionary MAP filter," *J. of Global Optimization*, vol. 37, no. 3, pp. 381-403, 2007.
33. P. Jensfelt and S. Kristensen, "Active global localisation for a mobile robot using multiple hypothesis tracking," *IEEE Transactions on Robotics and Automation*, vol. 17, no. 5, pp. 748-760, October 2001.
34. K. O. Arras, J. A. Castellanos, M. Schilt, and R. Siegwart, "Feature-based multi-hypothesis localization and tracking using geometric constraints," *Robotics and Autonomous Systems*, vol. 44, no. 1, pp. 41-53, 2003.
35. W. Burgard, D. Fox, D. Hennig, and T. Schmidt, "Estimating the absolute position of a mobile robot using position probability grids," in *AAAI/IAAI, Vol.* 2, 1996.
36. F. Dellaert, D. Fox, W. Burgard, and S. Thrun, "Monte Carlo localization for mobile robots," in *IEEE International Conference on Robotics and Automation (ICRA99)*, May 1999.
37. Z. Zhang, "Adaptive region intensity based rigid ultrasound and CT image registration," in *Computer Vision and Pattern Recognition, 2008. CVPR 2008. IEEE Conference on*, June 2008, pp. 1-7.
38. H. Munim and A. Farag, "A new global registration approach of medical imaging using vector maps," in *Biomedical Imaging: From Nano to Macro, 2007. ISBI 2007. 4th IEEE International Symposium on*, April 2007, pp. 584-587.
39. M. H. Moghari and P. Abolmaesumi, "Global registration of multiple bone fragments using statistical atlas models: Feasibility experiments," in *Engineering in Medicine and Biology Society, 2008. EMBS 2008. 30th Annual International Conference of the IEEE*, August 2008, pp. 5374-5377.
40. C. Fookes, J. Williams, and M. Bennamoun, "Global 3D rigid registration of medical images," in *Image Processing, 2000. Proceedings. 2000 International Conference on*, 2000, vol. 2, pp. 447-450.
41. R. Shinohara, K. Mori, D. Deguchi, T. Kitasaka, Y. Suenaga, H. Takabatake, M. Mori, and H. Natori, "Branch identification method for CT-Guided bronchoscopy based on eigenspace image matching between real and virtual bronchoscopic images," in *SPIE Medical Imaging 2006: Physiology, Function, and Structure from Medical Images*, A. Manduca and A. A. Amini, Eds., March 2006, vol. 6143, pp. 385-396.
42. J. P. Helferty, C. Zhang, G. McLennan, and W. E. Higgins, "Videoendoscopic distortion correction and its application to virtual guidance of endoscopy," *IEEE Trans. Med. Imaging*, vol. 20, no. 7, pp. 605-617, July 2001.
43. M. W. Graham, J. D. Gibbs, D. C. Cornish, M. Khan, R. Bascom, and W. E. Higgins, "Image-guided peripheral bronchoscopy: A pilot human study," *Chest*, under review, 2009.
44. W. E. Lorensen and H. E. Cline, "Marching cubes: A high resolution 3D surface construction algorithm," *Computer Graphics*, vol. 21, no. 4, pp. 163-169, July 1987.
45. R. S. Wright, Jr., and B. Lipchak, *OpenGL Super Bible, 3rd. Ed.*, SAMS Publishing, 2005.
46. G. Weifi, C. Wetzler, and E. V. Puttkamer, "Keeping track of position and orientation of moving indoor systems by correlation of range-finder scans," in *In Proc. 1994 IEEE Int. Conf on Intelligent Robots and Systems IROS '94*, 1994, pp. 595-601.
47. J. L. Bentley, F. P. Preparata, and M. G. Faust, "Approximation algorithms for convex hulls," *Commun. ACM*, vol. 25, no. 1, pp. 64-68, 1982.

The invention claimed is:

1. A global registration system useful in bronchoscopic guidance and other applications, comprising:
    a memory storing virtual bronchoscopy (VB) renderings of a 3D airway tree, the renderings including VB views and branch positions within the airway tree;
    a computer operative to search and analyze the VB renderings to identify the VB view and branch position that most closely matches a real bronchoscopic (RB) view from a bronchoscope of an unknown or arbitrary location along an unknown or arbitrary airway branch of the airway tree; and wherein the computer is operative to perform a search across at least a plurality of airway branches in the airway tree and wherein the search comprises:
        an intra-branch search within each airway branch of the plurality of airway branches of the airway tree to identify an optimal VB view along each airway branch of the plurality of airway branches of the airway tree that matches the received RB view, wherein the intra-branch search within each branch scans through a plurality of pre-defined view positions in that branch; and
        an inter-branch search subsequent to the intra-branch searches in which at least one of the optimal VB views from all of the intra-branch searches that most closely matches the RB view is identified and used for determining a 3D position of the bronchoscope; and
    a display presenting the 3D position of a bronchoscope within the airway tree based upon the VB view and branch position identified in the VB view.

2. The system of claim 1, wherein the computer is operative to identify a plurality of most likely branch positions having VB views closest to the received RB view.

3. The system of claim 1, wherein the computer uses domain-specific information regarding general bronchoscope position within the airway tree.

4. The system of claim 3, wherein the domain-specific information includes current lung designation or lung lobar position.

5. The system of claim 1, wherein the computer is operative to identify an optimum branch position having a VB view closest to each of a plurality of RB views, and wherein the multiple RB views are associated with the same or multiple branch positions within an airway tree.

6. The system of claim 1, wherein the intra-branch search performed by the computer comprises a fast search over all the branches in a global airway-bifurcation search space using a weighted normalized sum of squares distance metric to determine a best match.

7. The system of claim 1, wherein the intra-branch search performed by the computer comprises using pre-computed lumen region enclosing rectangles and a fast local registration refinement.

8. The system of claim 1, wherein the intra-branch search performed by the computer is carried out along a centerline of each airway branch.

9. The system of claim 1, wherein the matched VB view and RB view are correlated to a bifurcation feature.

10. The system of claim 1, wherein the computer is further operative to match the VB view and the RB view along the airway branches including portions of the airway branches between bifurcations.

11. The system of claim 7, wherein a best rendering position is provided corresponding to each optimal view from each intra-branch search and different roll angles are applied to the best rendering position to obtain different rendering positions, and wherein the local registration refinement includes adjusting the different rendering positions using an inverse compositional method for local registration.

* * * * *